United States Patent
Wong

(10) Patent No.: US 8,293,783 B2
(45) Date of Patent: Oct. 23, 2012

(54) USE OF ARTEMISININ DERIVATIVES FOR THE TREATMENT OF ASTHMA AND CHRONIC OBSTRUCTIVE PULMONARY DISEASE (COPD)

(75) Inventor: Wai Shiu Fred Wong, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 13/258,804

(22) PCT Filed: Mar. 24, 2010

(86) PCT No.: PCT/SG2010/000111
§ 371 (c)(1),
(2), (4) Date: Sep. 22, 2011

(87) PCT Pub. No.: WO2010/110747
PCT Pub. Date: Sep. 30, 2010

(65) Prior Publication Data
US 2012/0015922 A1    Jan. 19, 2012

Related U.S. Application Data

(60) Provisional application No. 61/162,868, filed on Mar. 24, 2009.

(51) Int. Cl.
*A61K 31/335* (2006.01)
*A61K 31/56* (2006.01)
(52) U.S. Cl. ........................ 514/450; 514/171
(58) Field of Classification Search ............. 514/450, 514/171
See application file for complete search history.

(56) References Cited

U.S. PATENT DOCUMENTS

| | | |
|---|---|---|
| 2002/0169140 A1 | 11/2002 | Prendergast |
| 2005/0096369 A1 | 5/2005 | Hoang |
| 2006/0084675 A1 | 4/2006 | Efferth et al. |

FOREIGN PATENT DOCUMENTS

| | | |
|---|---|---|
| EP | 1658844 | 5/2006 |
| WO | 2006/051987 A1 | 5/2006 |
| WO | 2010/009428 A1 | 1/2010 |

OTHER PUBLICATIONS

International Search Report and Written Opinion for PCT/SG2010/000111, mailed May 17, 2010.
International Preliminary Report on Patentability for PCT/SG2010/000111, mailed Jun. 24, 2011.

*Primary Examiner* — Jennifer M Kim
(74) *Attorney, Agent, or Firm* — Wolf, Greenfield & Sacks, P.C.

(57) ABSTRACT

Artesunate is a derivative of artemisinin isolated from a Chinese herb *Artemisia annua* L. It is used clinically for the treatment of malaria. We investigated potential anti-inflammatory actions of artemisinin derivatives. artemisinin derivatives significantly inhibited OVA-induced signs, symptoms and parameter of airway disorders Taken together, our results clearly demonstrate anti-inflammatory effects of artemisinin derivatives. Artemisinin derivatives can be used to complement or to replace oral steroids during asthma exacerbation treatment. Further artemisinin derivatives can be used as an anti-inflammatory agent for controlling airway disorders.

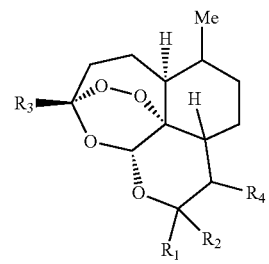

11 Claims, 11 Drawing Sheets

A

B

C

USE OF ARTEMISININ DERIVATIVES FOR THE TREATMENT OF ASTHMA AND CHRONIC OBSTRUCTIVE PULMONARY DISEASE (COPD)

CROSS-REFERENCE TO RELATED APPLICATION

This application is a national stage filing under 35 U.S.C. §371 of international PCT application, PCT/SG2010/000111, filed Mar. 24, 2010, which claims priority under 35 U.S.C. §119(e) to U.S. provisional patent application, U.S. Ser. No. 61/162,868, filed Mar. 24, 2009, each of which is incorporated herein by reference.

FIELD

The invention relates to the use of artemisinin derivatives such as artesunate compounds for the treatment of asthma and chronic obstructive pulmonary disease.

BACKGROUND

At present, there are about 300 million people worldwide suffering from asthma. It is predicted that the prevalence will go up to 400 million in 2025. Currently, there are three anti-inflammatory agents for controlling asthma, which include inhaled steroids, cysteinyl-leukotriene receptor antagonist and cromolyn. However, the therapeutic efficacies of cysteinyl-leukotriene receptor antagonist and cromolyn are highly variable and may be limited to certain subgroup of patients. In addition, 5-10% of the asthmatics are not well-controlled by current drug treatment and they require oral steroids during exacerbation. Oral steroid usage is commonly associated with adverse effects.

Allergic asthma is a chronic airway disorder characterized by airway inflammation, mucus hypersecretion, and airway hyperresponsiveness (AHR) (1). Cumulative evidence revealed that these inflammatory responses are mediated by T-helper type 2 (Th2) cells together with mast cells, B cells and eosinophils, as well as a number of inflammatory cytokines and chemokines (1, 2). IL-4 is imperative for B cell isotype switching for the synthesis of immunoglobulin (Ig)E. Allergen-induced cross-linking of IgE-bound high affinity IgE receptors (FcεRI) on the surface of mast cells leads to degranulation and activation of mast cells, and the release of inflammatory mediators like histamine, leukotrienes and cytokines, and immediate bronchoconstriction (3, 4). IL-5 is vital for the growth, differentiation, recruitment, and survival of eosinophils which contribute to inflammation and even airway remodeling in asthma (5). IL-13 plays a pivotal role in the effector phase of Th2 responses such as eosinophilic inflammation, mucus hypersecretion, AHR and airway remodeling (6). In addition, chemokines such as RANTES (regulated on activation, normal T cells expressed and secreted) and eotaxin are crucial to the delivery of eosinophils to the airways (7). Airway eosinophilia, together with Th2 cytokines IL-4, IL-5 and IL-13, may ultimately contribute to AHR in asthma (8).

Chronic obstructive pulmonary disease (COPD) refers to chronic bronchitis and emphysema, two commonly co-existing diseases of the lungs in which the airways become narrowed (14). This leads to a limitation of the flow of air to and from the lungs causing shortness of breath. In contrast to asthma, the limitation of airflow is poorly reversible and usually gets progressively worse over time.

COPD is caused by noxious particles or gas, most commonly from tobacco smoking, which triggers an abnormal inflammatory response in the lung. The natural course of COPD is characterized by occasional sudden worsening of symptoms called acute exacerbations, most of which are caused by infections or air pollution. COPD is also known as chronic obstructive lung disease (COLD), chronic obstructive airway disease (COAD), chronic airflow limitation (CAL) and chronic obstructive respiratory disease (CORD).

There is currently no cure for COPD and the only measures that have been shown to reduce mortality are smoking cessation and supplemental oxygen (14). COPD can be managed with bronchodilators such as $\beta_2$ agonists and/or anticholinergics. $\beta_2$ agonist stimulate $\beta_2$ receptors while anticholinergics block stimulation from cholinergic nerves both are medicines that relax smooth muscle around the airways, increasing air flow. There are several $\beta_2$ agonists available, salbutamol or albuterol and terbutaline are widely used short acting $\beta_2$ agonists and provide rapid relief of COPD symptoms. Long acting $\beta_2$ agonists (LABAs) such as salmeterol and formoterol are used as maintenance therapy. Ipratropium is the most widely prescribed short acting anticholinergic drug. Anticholinergics appear to be superior to $\beta_2$ agonists in COPD, however both $\beta_2$ agonists and anticholinergics do not have anti-inflammatory actions and they do not halt progression of COPD.

PI3K is a family of lipid kinases comprising of 8 isoforms divided into 3 classes, of which class I enzymes are specific in phosphorylating phosphatidylinositol-4,5-bisphosphate (PIP2) to generate phosphatidylinositol-3,4,5-trisphosphate (PIP3), an ubiquitous second messenger that serves as a docking site for the activation of pleckstrin homology domain-containing kinases such as Akt. Class I PI3Ks are divided into class IA and class IB, and exist as heterodimers with catalytic subunits of class IA (p110α, p110β, and p110δ) and of class IB (p110γ) binding to regulatory subunits of class IA (p85α, p85β, p55γ, p55β or p50α) and of class IB (p101 or p84/p87), respectively (38). Of these, p110δ and p110γ PI3Ks are enriched in leukocytes and have been shown to play a critical role in the activation, proliferation, differentiation and migration of T and B lymphocytes, mast cells and eosinophils (18-20).

Artesunate is a semi-synthetic derivative of artemisinin, a sesquiterpene trioxane lactone isolated from the herb *Artemisia annua*. This medicinal plant has been used as a remedy for fevers and chills for centuries in China (9). Artemisinin derivatives including artesunate are anti-malarial drugs effective for both uncomplicated and severe malaria (9, 10). Besides this, Artemisinin derivatives have been shown to possess anti-cancer (11, 12), anti-viral (13), and anti-inflammatory (15 and 17) activities. Artesunate has been reported to block the production of IL-1β, IL-6 and IL-8 from TNF-α-stimulated human rheumatoid arthritis fibroblast-like synoviocytes (14). In addition, artesunate inhibits lipopolysaccharide-induced production of TNF-α, IL-6 and nitric oxide (NO), and expression of toll-like receptor 4 (TLR4) and TLR9 from macrophages (16, 18). The exact molecular mechanism that mediates these anti-inflammatory effects by artesunate has not been unequivocally determined. There are some evidence pointing to the inhibition of nuclear factor (NF)-κB transcriptional activity by artesunate and other artemisinin derivatives (15-17). More recently, artesunate has been found to possess strong inhibitory activity against the phosphoinositide 3-kinase (PI3K)/Akt signaling pathway (12-14).

Artesunate is a derivative of artemisinin isolated from a Chinese herb *Artemisia annua* L. It is used clinically for the treatment of malaria. The structure of artesunate is depicted in FIG. 1. Artesunate is a well-tolerated drug approved for malaria therapy and, moreover, has an excellent safety profile demonstrated by extensive use as a malaria treatment.

SUMMARY

We propose to use artemisinin derivatives such as artesunate for the treatment of airway disorders such as asthma, an asthma exacerbation or COPD as a controller. We propose to use artemisinin derivatives such as artesunate to complement steroids treatment or replace steroid treatment during asthma exacerbation.

Artemisinin derivatives such as artesunate appear to dose dependently inhibit the development of airway obstruction.

Accordingly, a first aspect of the invention comprises a compound comprising an artemisinin derivative for use in the treatment of an airway disorder comprising administering to a subject in need thereof an effective amount of the compound. In one embodiment the artemisinin derivative comprises formula (2).

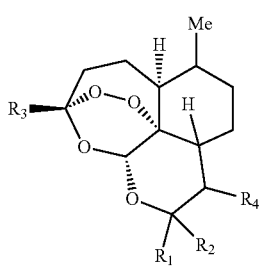

(2)

wherein $R_1$ and $R_2$ taken together form a carbonyl (=O), and $R_3$ and $R_4$ are independently H, or an optionally substituted group selected from a substituted or non-substituted alkyl, a substituted or non-substituted aryl, a substituted or non-substituted heteroaryl, a substituted or non-substituted arylalkyl, and a substituted or non-substituted heteroarylalkyl or a pharmaceutically acceptable salt or ester thereof; or wherein $R_1$ is H, and $R_2$ is —OA, wherein A is H or an optionally substituted group selected from a substituted or non-substituted alkyl, a substituted or non-substituted aryl, a substituted or non-substituted heteroaryl, a substituted or non-substituted arylalkyl, and a substituted or non-substituted heteroarylalkyl; or a pharmaceutically acceptable salt or ester thereof and $R_3$ and $R_4$ are independently H or an optionally substituted group selected from a substituted or non-substituted alkyl, a substituted or non-substituted aryl, a substituted or non-substituted heteroaryl, a substituted or non-substituted arylalkyl, and a substituted or non-substituted heteroarylalkyl; or a pharmaceutically acceptable salt or ester thereof. Preferably the artemisinin derivative of formula (2) is selected from the group consisting of artemisinin, dihydroartemisinin, artemether, artemotil, artelinic acid, arteether, and artesunate.

In one embodiment $R_1$ and $R_2$ taken together form a C1-C6 carbonyl and $R_3$ and $R_4$ are independently H or an optionally substituted C1-C10 alkyl. Preferably the artemisinin derivative is artesunate.

In one embodiment the airway disorder is asthma and the artemisinin derivative is for use in treating asthma. In another embodiment the airway disorder is chronic obstructive pulmonary disease (COPD) and the artemisinin derivative is for use in treating COPD.

In another embodiment the airway disorder is an airway exacerbation and the artemisinin derivative is for use in treating or preventing or controlling the airway exacerbation.

Another aspect of the invention comprises a method of treating or preventing or controlling an airway disorder comprising administering a dose of an artemisinin derivative.

In one embodiment the artemisinin derivative comprises formula (2) as described above. In one embodiment the method may further comprise administering a composition of an effective amount of steroids such as corticosteroids in combination with the artemisinin derivative. Preferably the composition is adapted for inhalation.

Another aspect of the invention comprises a kit to treat an airway disorder comprising the artemisinin derivative of the invention.

In one embodiment the kit may further comprise a steroid.

Another aspect of the invention comprises a composition comprising the artemisinin derivative in combination with a steroid.

In one embodiment the artemisinin derivative of the composition is formula (2) as described above. In another embodiment the groups of formula (2) are, $R_1$ and $R_2$ taken together form a C1-C6 carbonyl and $R_3$ and $R_4$ are independently H or an optionally substituted C1-C10 alkyl.

In one embodiment the artemisinin derivative of the composition of may be selected from the group consisting of artemisinin, dihydroartemisinin, artemether, artemotil, artelinic acid, arteether, and artesunate. Preferably the artemisinin derivative is artesunate.

The steroid of the composition may be a corticosteroid. Preferably selected from Dexamethasone, Budesonide, Fluticasone, Ciclesonide, or Beclomethasone Dipropionate.

In one embodiment the composition is suitable for use in treating or preventing or controlling an airway disorder such as, asthma, chronic obstructive pulmonary disease or the like. Preferably the composition may be adapted for inhalation.

BRIEF DESCRIPTION OF THE DRAWINGS

The invention will be better understood by reference to the following description of several specific embodiments thereof as shown in the accompanying drawings in which.

DETAILED DESCRIPTION

Airway disorders such as COPD, allergic airway inflammation and airway hyperresponsiveness (AHR) development involve multiple inflammatory cells and a wide array of mediators. We report here for the first time that the antimalarial agent artemisinin derivatives effectively reduced OVA-induced inflammatory cell recruitment into BAL fluid, IL-4, IL-5, IL-13 and eotaxin production, serum IgE synthesis, pulmonary eosinophilia, mucus hypersecretion and AHR in a mouse asthma model potentially via inhibition of the PI3K/Akt signaling pathway. Our present findings support a novel therapeutic use of artemisinin derivatives in the treatment of airway disorders.

We propose to use artemisinin derivatives to complement or to replace oral steroids during airway disorders such as asthma exacerbation. We propose to use artemisinin derivatives as an anti-inflammatory agent for controlling airway disorders such as asthma.

Compounds of the Invention

"Compounds" include known artemisinin derivatives including artemisinin, dihydroartemisinin, artemether, artemotil, arteether, artelinic acid, and artesunate. Preferred compounds are a pharmaceutical composition including such a compound of Formula (2).

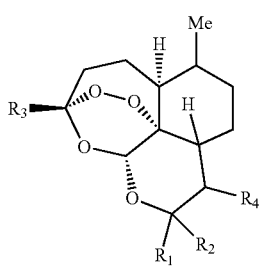

(2)

In one embodiment $R_1$ and $R_2$ taken together form a carbonyl (=O), and $R_3$ and $R_4$ are independently H or an optionally substituted group selected from a substituted or unsubstituted alkyl, a substituted or unsubstituted aryl, a substituted or unsubstituted heteroaryl, a substituted or unsubstituted arylalkyl, and a substituted or unsubstituted heteroarylalkyl; or a pharmaceutically acceptable salt or ester thereof;

In another embodiment $R_1$ is H, and $R_2$ is substituted or non-substituted —OA, wherein A is H or an optionally substituted group selected from a substituted or unsubstituted alkyl, a substituted or unsubstituted aryl, a substituted or unsubstituted heteroaryl, a substituted or unsubstituted arylalkyl, and a substituted or unsubstituted heteroarylalkyl; or a pharmaceutically acceptable salt or ester thereof and $R_3$ and $R_4$ are independently H or an optionally substituted group selected from a substituted or unsubstituted alkyl, a substituted or unsubstituted aryl, a substituted or unsubstituted heteroaryl, a substituted or unsubstituted arylalkyl, and a substituted or unsubstituted heteroarylalkyl; or a pharmaceutically acceptable salt or ester thereof. Preferably the artemisinin derivative of formula (2) is selected from the group consisting of artemisinin, dihydroartemisinin, artemether, artemotil, artelinic acid, arteether, and artesunate.

Figure 1:
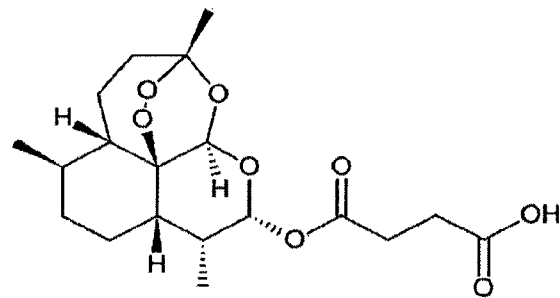
FIG. 1: chemical depiction of the structure of Artesunate.

In one embodiment $R_1$ and $R_2$ taken together form a C1-C6 carbonyl, and $R_3$ and $R_4$ are independently H or an optionally substituted C1-C10 alkyl. In a preferred embodiment the artemisinin derivative is artesunate of Formula (1) as depicted in FIG. 1.

In some embodiments of the invention, the artemisinin derivative is selected from the group consisting of artemisinin, dihydroartemisinin, artemether, artemotil, arteether, artelinic acid, and artesunate.

In some embodiments, at least one of $R_1$ and $R_2$ is H, and $R_3$ and $R_4$ are independently substituted or unsubstituted alkyl.

In some embodiments $R_1$ and $R_2$ taken together comprise a carboxyl such as a carboxylic acid, the compounds of formula (2) are used as salts or esters of the carboxylic acid. In some embodiments, the ester is a simple alkyl ester such as a $C_1$-$C_6$ alkyl ester, where the $C_1$-$C_6$ alkyl is optionally substituted with one or more halo, hydroxyl, or $C_1$-$C_4$ alkoxy groups. Where the compound of formula (2) is an ester, it is sometimes a methyl or ethyl or propyl or butyl ester, or a 2-methoxyethyl ester or an ethylene glycol ester.

The compounds of formula (2) can be used to treat subjects afflicted with a variety of airway disorders.

As used herein, the terms "alkyl", "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as $C_1$-$C_{10}$ or C1-10. When heteroatoms (N, O and S typically) are allowed to replace carbon atoms as in heteroalkyl groups, for example, the numbers describing the group, though still written as e.g. $C_1$-$C_6$, represent the sum of the number of carbon atoms in the group plus the number of such heteroatoms that are included as replacements for carbon atoms in the ring or chain being described.

Typically, the alkyl, alkenyl and alkynyl substituents of the invention contain 1-10C (alkyl), or 2-10C (alkenyl or alkynyl). Alternatively, they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often substituted to the extent that such substitution makes sense chemically. Typical substituents include, but are not limited to, halo, —O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, $C_1$-$C_8$ alkyl, $C_2$-$C_8$ heteroalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each R is optionally substituted with halo, =O, =N—CN, =N—OR', =NR', OR', NR'$_2$, SR', $SO_2$R', $SO_2$NR'$_2$, NR$^5$$SO_2$R', NR'CONR'$_2$, NR'COOR', NR'COR', CN, COOR', CONR'$_2$, OOCR', COR', and $NO_2$, wherein each R' is independently H, $C_1$-$C_8$ alkyl, $C_2$-$C_8$ heteroalkyl, $C_1$-$C_8$ acyl, $C_2$-$C_8$ heteroacyl, $C_6$-$C_{10}$ aryl or $C_5$-$C_{10}$ heteroaryl. Alkyl, alkenyl and alkynyl groups can also be substituted by $C_1$-$C_8$ acyl, $C_2$-$C_8$ heteroacyl, $C_6$-$C_{10}$ aryl or $C_5$-$C_{10}$ heteroaryl, each of which can be substituted by the substituents that are appropriate for the particular group.

While "alkyl" as used herein includes cyclo-alkyl and cyclo-alkylalkyl groups, the term "cyclo-alkyl" may be used herein to describe a carbo-cyclic non-aromatic group that is connected via a ring carbon atom (i.e., its open valence for connecting to a molecule is on a ring carbon), and "cycloalkylalkyl" may be used to describe a carbocyclic non-aromatic group that is connected to the molecule through an alkylene linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom (—C(O)—), and heteroacyl refers to the corresponding groups wherein at least one carbon other than the carbonyl carbon has been replaced by a heteroatom chosen from N, O and S. The other open valence of the carbonyl is available to connect the acyl group or heteroacyl group to a base molecule. Thus heteroacyl includes, for example, —C(=O)OR and —C(=O)$NR_2$ as well as —C(=O)— heteroaryl.

Acyl and heteroacyl groups are bonded to any group or molecule to which they are attached through the open valence of the carbonyl carbon atom. Typically, they are $C_1$-$C_8$ acyl groups, which include formyl, acetyl, pivaloyl, and benzoyl, and $C_2$-$C_8$ heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic $C_5$-$C_6$ aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including $C_1$-$C_8$ alkyl, $C_2$-$C_8$ alkenyl, $C_2$-$C_8$ alkynyl, $C_5$-$C_{12}$ aryl, $C_1$-$C_8$ acyl, and heteroforms of these, each of which can itself be further substituted; other substituents for aryl and heteroaryl moieties include halo, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, $C_1$-$C_8$ alkyl, $C_2$-$C_8$ alkenyl, $C_2$-$C_8$ alkynyl, $C_6$-$C_{10}$ aryl, $C_5$-$C_{10}$ heteroaryl, $C_7$-$C_{12}$ arylalkyl, or $C_6$-$C_{12}$ heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is $C_1$-$C_8$ alkyl or a hetero form thereof. These linkers may also include a carbonyl group, thus making them able to provide substituents as an acyl or heteroacyl moiety. An aryl or heteroaryl ring in an arylalkyl group may be substituted with the same substituents described above for aryl groups. Preferably, an arylalkyl group includes a phenyl ring optionally substituted with the groups defined above for aryl groups and a $C_1$-$C_4$ alkylene that is unsubstituted or is substituted with one or two $C_1$-$C_4$ alkyl groups, where the alkyl groups can optionally cyclize to form a ring such as cyclopropane, dioxolane, or oxacyclopentane. Similarly, a heteroarylalkyl group preferably includes a $C_5$-$C_6$ monocyclic heteroaryl group that is optionally substituted with the groups described above as substituents typical on aryl groups and a $C_1$-$C_4$ alkylene that is unsubstituted or is substituted with one or two $C_1$-$C_4$ alkyl groups, or it includes an optionally substituted phenyl ring or $C_5$-$C_6$ monocyclic heteroaryl and a $C_1$-$C_4$ heteroalkylene that is unsubstituted or is substituted with one or two $C_1$-$C_4$ alkyl groups, where the alkyl groups can optionally cyclize to form a ring such as cyclopropane, dioxolane, or oxacyclopentane.

Where an arylalkyl group is described as optionally substituted, the substituents may be on either the alkyl portion or on the aryl or heteroaryl portion of the group. The substituents optionally present on the alkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a $C_7$-arylalkyl group, and phenylethyl is a $C_8$-arylalkyl.

"Alkylene" as used herein refers to a divalent hydrocarbyl group; because it is divalent, it can link two other groups together. Sometimes it refers to —$(CH_2)_n$— where n is 1-8 and preferably n is 1-4, though where specified, an alkylene can also be substituted by other groups, and can be of other lengths. The open valences of an alkylene need not be at opposite ends of a chain. Thus —CH(Me)— and —C(Me)$_2$— are also included within the scope of the term 'alkylenes', as are cyclic groups such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, R' is alkyl, this alkyl may optionally be substituted by the remaining substituents listed as embodiments for R' where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. In some embodiments, the number of substituents permitted on a group is equal to the number of carbon atoms in the group. Where an optional substituent is attached via a double bond, such as a carbonyl oxygen (=O), the group occupies two available valences, so the total number of other substituents that may be included is reduced according to the number of other available valences.

"Halo", as used herein includes fluoro, chloro, bromo and iodo. Fluoro and chloro are often preferred.

"Pharmaceutically acceptable salt" as used herein refers to a protonated or deprotonated form of a compound, such as a compound of formula (2), that is accompanied by a counter ion, where the counter ion is not harmful to a subject to be treated. Many counter ions suitable for inclusion in pharmaceutically acceptable salts are known in the art. In many embodiments of the compounds of formula (2), the compound comprises a carboxylic acid; for such compounds, a salt can be formed by de-protonation of the carboxylic acid to form a carboxylate. The carboxylate will be accompanied by a counter ion, and for making a pharmaceutically acceptable salt, the counter ion is selected to have minimal toxicity or adverse effect on the subject to be treated. Examples of counter ions for pharmaceutically acceptable salts of such carboxylates or other de-protonated species include, but are not limited to, so sodium, magnesium, potassium, calcium, iron, zinc, ammonium, alkylammonium, imidazolium, and the like.

Treatment Methods

Treatment" and "treat" and synonyms thereof refer to both therapeutic treatment and prophylactic or preventative measures, wherein the object is to prevent or slow down (lessen) an airway disorder.

As used herein a "therapeutically effective amount" of a compound will be an amount of active agent that is capable of treating, preventing or at least slowing down (lessening) an airway disorder. Dosages and administration of an antagonist of the invention in a pharmaceutical composition may be determined by one of ordinary skill in the art of clinical pharmacology or pharmacokinetics. An effective amount of the compound or composition to be employed therapeutically will depend, for example, upon the therapeutic objectives, the route of administration, and the condition of the mammal. Accordingly, it will be necessary for the therapist to titer the dosage and modify the route of administration as required to obtain the optimal therapeutic effect. A typical daily dosage might range from about 10 ng/kg to up to 100 mg/kg of the mammal's body weight or more per day, preferably about 1 µg/kg/day to 10 mg/kg/day.

"Subject" for the purposes of the present invention includes humans and other animals, particularly mammals. Thus the methods are applicable to both human therapy and veterinary applications. In certain embodiments the subject is a mammal, and in a preferred embodiment the subject is human.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age and weight of the patient to be treated, and the like. The therapeutically effective amount can be determined routinely by one of ordinary skill in the art having regard to their knowledge and to this disclosure.

The compounds of the invention can be made by isolation from a Chinese herb *Artemisia annua* L. Alternatively the compound may be biosynthesised in yeast or *E. coli* using methods well known in the art. Other synthetic methods of manufacture are disclosed in U.S. Pat. No. 4,992,561 and WO2009/088404 which are incorporated herein by reference.

Compositions of the Invention

Compounds produced according to the invention can be administered for the treatment of airway disorders in the form of pharmaceutical compositions.

Thus, the present invention also relates to compositions including pharmaceutical compositions comprising a therapeutically effective amount of an artemisinin derivative. As used herein a compound will be therapeutically effective if it is able to affect the measured parameters of airway inflammation.

In a preferred embodiment the compounds and compositions are adapted to be administered to the lungs directly through the airways by inhalation. Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose or starch. Inhalable dry powder compositions may be presented in capsules and cartridges of gelatin or a like material, or blisters of laminated aluminium foil for use in an inhaler or insufflator. Each capsule or cartridge may generally contain between 20 pg-10 mg of the active compound. Alternatively, the compound of the invention may be presented without excipients.

The inhalable compositions may be packaged for unit dose or multi-dose delivery. For example, the compositions can be packaged for multi-dose delivery in a manner analogous to that described in GB 2242134, U.S. Pat. Nos. 6,632,666, 5,860,419, 5,873,360 and 5,590,645 (all illustrating the "Diskus" device), or GB2178965, GB2129691, GB2169265, U.S. Pat. Nos. 4,778,054, 4,811,731 and 5,035,237 (which illustrate the "Diskhaler" device), or EP 69715 ("Turbuhaler" device), or GB 2064336 and U.S. Pat. No. 4,353,656 ("Rotahaler" device).

Spray compositions for topical delivery to the lung by inhalation may be formulated as aqueous solutions or suspensions or as aerosols delivered from pressurised packs, such as a metered dose inhaler (MDI), with the use of a suitable liquefied propellant. The medication in pressurized MDI is most commonly stored in solution in a pressurized canister that contains a propellant, although it may also be a suspension.

Aerosol compositions suitable for inhalation can be presented either as suspensions or as solutions and typically contain the active compound and a suitable propellant such as a fluorocarbon or hydrogen-containing chlorofluorocarbon or mixtures thereof, particularly hydrofluoroalkanes such as dichlorodifluoromethane, trichlorofluoromethane, dichlorotetrafluoroethane, and especially 1,1, 1, 2-tetrafluoroethane, 1,1, 1,2, 3,3, 3-heptafluoro-n-propane and mixtures thereof.

The aerosol composition may optionally contain additional excipients typically associated with such compositions, for example surfactants such as oleic acid or lecithin and cosolvents such as ethanol. Pressurised formulations will generally be contained within a canister (for example an aluminium canister) closed with a metering valve and fitted into an actuator provided with a mouthpiece.

Medicaments for administration by inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes the particles of the active ingredient may be subjected to a size reducing process such as micronisation. The desired size fraction may be separated out by air classification or sieving. Preferably, the particles will be crystalline. When an excipient such as lactose is employed, typically the particle size of the excipient will be much greater than the particle size of the active ingredient.

Intranasal sprays may be formulated with aqueous or non-aqueous vehicles with the addition of agents such as thickening agents, buffer salts or acid or alkali to adjust the pH, isotonic adjusting agents or anti-oxidants.

Solutions for inhalation by nebulisation may be formulated with an aqueous vehicle with the addition of agents such as acid or alkali, buffer salts, isotonic adjusting agents or antimicrobial agents. They may be sterilised by filtration or heating in an autoclave, or presented as a non-sterile product. Nebulizers supply the aerosol as a mist created from an aqueous formulation.

In one embodiment, the artemisinin derivative is incorporated into a composition with supplementary active ingredients. Preferably the supplementary active ingredients are anti-inflammatory agents or inhaled steroids, corticosteroids cysteinyl-leukotriene receptor antagonist and cromolyn and or bronchodilators such as) $\beta_2$ agonists and/or anticholinergics. Some inhaled steroids may include Dexamethasone, Budesonide (PULMICORT®), Fluticasone (FLOVENT®), Ciclesonide (ALVESCO®), Beclomethasone Dipropionate (QVAR®) or others known in the art. $\beta_2$ agonists may include salbutamol, albuterol, terbutaline, salmeterol, or formoterol. An anticholinergic may include Ipratropium.

In one particular embodiment the artemisinin derivative is administered from a dry powder inhaler.

In another embodiment, the artemisinin derivative is administered by an aerosol dispensing device, preferably in conjunction with an inhalation chamber such as the "Volumatic" (RTM) inhalation chamber.

Pharmaceutical forms of the invention suitable for injectable use include sterile aqueous solutions (where water soluble) or dispersions and sterile powders for the extemporaneous preparation of sterile injectable solutions and or one or more carrier. Alternatively, injectable solutions may be delivered encapsulated in liposomes to assist their transport across cell membrane. The composition must be stable under the conditions of manufacture and storage and must be preserved against the contaminating/destructive action of microorganisms such as, for example, bacteria and fungi.

The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as, for example, lecithin, by the maintenance of the required particle size in the case of dispersion and by the use of surfactants. Preventing the action of microorganisms in the compositions of the invention is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and freeze-drying, to yield a powder of the active ingredient plus any additional desired ingredient from previously sterile-filtered solution thereof.

When the active ingredients, in particular small molecules contemplated within the scope of the invention, are suitably protected they may be orally administered, for example, with an inert diluent or with an edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that a dosage unit form contains between about 0.1 μg and 20 g of active compound.

The tablets, troches, pills, capsules and the like may also contain binding agents, such as, for example, gum, acacia, corn starch or gelatin. They may also contain an excipient, such as, for example, dicalcium phosphate. They may also contain a disintegrating agent such as, for example, corn starch, potato starch, alginic acid and the like. They may also contain a lubricant such as, for example, magnesium stearate. They may also contain a sweetening agent such a sucrose, lactose or saccharin. They may also contain a flavouring agent such as, for example, peppermint, oil of wintergreen, or cherry flavouring.

When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparaben as preservatives, a dye and flavouring such as, for example, cherry or orange flavour. Of course, any material used in preparing any dosage unit form should be pharmaceutically pure and substantially non-toxic in the amounts employed. In addition, the active compound(s) may be incorporated into sustained-release preparations and formulations.

To this extent the active ingredient may be held within a matrix which controls the release of the active agent. Preferably, the matrix comprises a substance selected from the group consisting of lipid, polyvinyl alcohol, polyvinyl acetate, polycaprolactone, poly(glycolic)acid, poly(lactic) acid, polycaprolactone, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly (ortho esters), sucrose acetate isobutyrate (SAIB), and combinations thereof and other polymers such as those disclosed in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety. Preferably, the matrix sustainedly releases the drug.

Pharmaceutically acceptable carriers and/or diluents may also include any and all solvents, dispersion media, coatings, antibacterials and/or antifungals, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated.

Supplementary active ingredients can also be incorporated into the compositions. Preferably those supplementary active ingredients are anti-inflammatory agents such as inhaled steroids, cysteinyl-leukotriene receptor antagonist and cromolyn and or bronchodilators such as $\beta_2$ agonists and/or anticholinergics. $\beta_2$ agonists may include salbutamol, albuterol, terbutaline, salmeterol, or formoterol. An anticholinergic may include Ipratropium.

It is especially advantageous to formulate parenteral compositions in dosage unit form for ease of administration and uniformity of dosage. Dosage unit form as used herein refers to physically discrete units suited as unitary dosages for the mammalian subjects to be treated, each unit containing a predetermined quantity of active material calculated to produce the desired therapeutic effect in association with the required pharmaceutical carrier. The dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.5 μg to about 2000 mg. Expressed in proportions, the active compound is generally present in from about 0.5 pg to about 2000 mg/ml of carrier. In the case of compositions containing supplementary active ingredients, the dosages are determined by reference to the usual dose and manner of administration of the said ingredients.

The compound or the composition may be in the form of a treatment kit comprising the dosage unit forms and instructions for use.

Parameters of Airway Inflammation

As discussed above airway disorders such as asthma and COPD development and or exacerbation is very complex, involving the interplay of proteins, kinases, cytokines, chemokines and other components known to interact with a range of related pathways. Based on some of the known interactions we measured the expression of several parameter that would be expected to be either increased or decreased during airway disorders in either the presence or the absence of the compounds of the invention.

Parameters of airway inflammation are well known in the art and include: measurement of bronchoalveolar lavage fluid inflammatory cell counts (both total and differential) and cytokine levels, analysis of pulmonary cell infiltration and mucus hypersecretion using histological approach, measurement of airway hyperresponsiveness, the clinical end point of a bronchospasm, and inflammatory biomarker analysis of the lung samples. Any one of these methods alone or in combination with one or more of the other methods listed or known in the art can be used to determine if the compounds successfully reduce airway inflammation.

Preferred Embodiments

Our findings reveal for the first time significant inhibition of Akt($ser_{473}$) phosphorylation and of its downstream kinases by artesunate in both OVA-challenged lungs in vivo and EGF-stimulated normal human bronchial epithelial cells in vitro. Taken together, we have established that anti-malarial drug artesunate, a semi-synthetic derivative of artemisinin isolated from the herb *Artemisia annua*, can effectively suppress various aspects of OVA-induced Th2-mediated allergic airway inflammation in mice via inhibition of the PI3K/Akt signaling pathway. Without being limited to any theory we hypothesise that artemisinin derivatives such as artesunate may attenuate allergic asthma via inhibition of the PI3KAkt signalling pathway. We show that artemisinin derivatives such as artesunate have a therapeutic value in the treatment of asthma and COPD. We investigated the effects of artesunate on various aspects of ovalbumin (OVA)-induced Th2-mediated allergic airway inflammation in an in vivo mouse asthma model and explored the anti-inflammatory mechanism of action of artesunate. Our results clearly indicate that artesunate attenuates allergic airway inflammation and it is likely mediated through inhibition of the PI3K/Akt signaling pathway.

We investigated potential anti-inflammatory actions of artesunate in a mouse asthma model. BALB/c mice sensitized and challenged with OVA developed airway eosinophilia and mucus hypersecretion, and elevations in serum IgE level and in bronchoalveolar lavage (BAL) fluid cytokine level. Artesunate significantly inhibited OVA-induced increases in BAL fluid eosinophil count, and IL-5 and IL-13 levels. It also reduced the serum level of OVA-specific IgE. Histologic analysis reveals that artesunate suppressed OVA-induced inflammatory cell infiltration and airway mucus production. Besides, artesunate markedly attenuated OVA-induced mRNA expression of ICAM-1, VCAM-1, Muc5ac and chitinases. Furthermore, artesunate inhibited TNF-α-induced phosphorylation of phosphoinositide 3-kinase (PI3K) and its downstream Akt and p70 S6 kinase, as well as nuclear factor (NF)-κB DNA binding activity in normal human bronchial epithelial cells. Taken together, our results clearly demonstrate anti-inflammatory effects of artesunate in a mouse asthma model, and it may act by inhibiting PI3K/Akt signaling pathway.

Our present results show that artesunate significantly reduced the level of IL-4, IL-5, IL-13 and eotaxin in BAL fluids from OVA-challenged mice. Artesunate was found to suppress OVA-induced phosphorylation of Akt and its downstream signaling molecules tuberin, p70S6K and 4E-BP1, and transactivation of NF-κB in lung samples. Therefore, the observed reduction of IL-4, IL-5, IL-13 and eotaxin levels in BAL fluid from artesunate treated mice may be due to inhibition of PI3K/Akt and its downstream kinases in the inflammatory and airway resident cells. Furthermore, our in vitro study using direct OVA stimulation of lymph node cells isolated from artesunate-treated mice produced markedly lower level of IL-4, IL-5 and IL-13 together with higher IFN-γ level as compared with DMSO-treated mice. These data show that the anti-inflammatory effect of artesunate is at least in part mediated through a direct suppressive action on T lymphocytes.

Figure 2A:
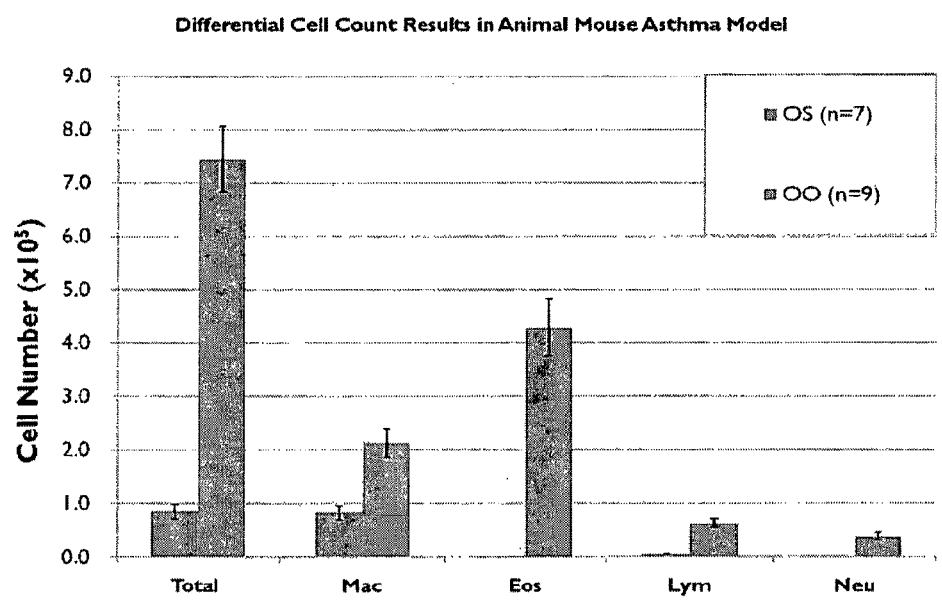
FIG. 2: Effects of artesunate on bronchoalveolar lavage fluid (BALF) cell infiltration. (Upper panel) Inflammatory cell counts in BALF obtained from sensitized mice 24 hours after the last saline aerosol (OS) or 10 mg/ml ovalbumin aerosol (OO) challenge. (Lower panel) Artesunate significantly reduced ovalbumin-induced inflammatory cell counts. Differential cell counts were performed on a minimum of 500 cells to identify eosinophil (Eos), macrophage (Mac), neutrophil (Neu), and lymphocyte (Lym).
Figure 2B:
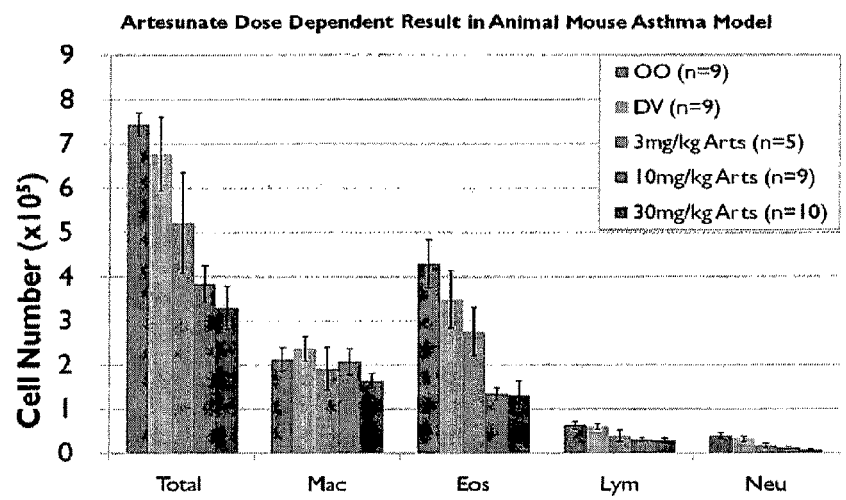
Figure 3:
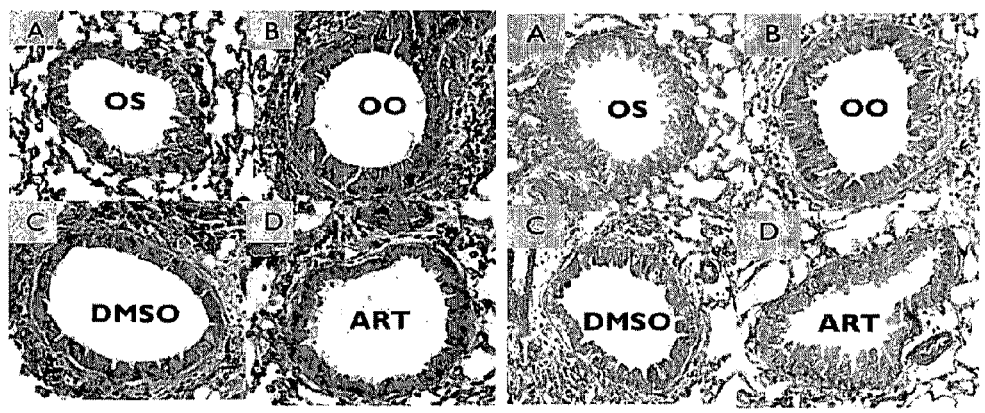
FIG. 3: Effects of artesunate on lung tissue eosinophilia and mucus production. Histologic examination of lung tissue eosinophilia (left panel, H&E staining, magnification ×400) and mucus secretion (right panel, PAS staining, magnification ×400) 24 hours after the last challenge of saline (OS), OVA aerosol (O), OVA aerosol plus DMSO (DMSO), or OVA aerosol plus 30 mg/kg artesunate (ART).

In our mouse asthma model using ovalbumin as aeroallergen, we showed that artesunate dose-dependently inhibited ovalbumin-induced cell infiltration into the airways obtained from bronchoalveolar lavage fluid and observed in formalin-fixed lungs as shown in FIG. 2 and FIG. 3. Further, artesunate dose dependently inhibited ovalbumin-induced increases in total cell count, eosinophil count, IL-4, IL-5, IL-13 and eotaxin levels in bronchoalveolar lavage fluid, and reduced serum level of ovalbumin-specific IgE. It attenuated ovalbumin-induced lung tissue eosinophilia and airway mucus production, mRNA expression of Eselectin, chitinases, IL-17, IL-33, Muc5ac and inducible nitric oxide synthase in lung tissues, and airway hyperresponsiveness to methacholine. In normal human bronchial epithelial cells, artesunate blocked epidermal growth factor-induced phosphorylation of Akt and its downstream substrates tuberin, p70S6 kinase and 4E-binding protein 1, and transactivation of nuclear factor (NF)-κB. Similarly, artesunate blocked the phosphorylation of Akt and its downstream substrates in lung tissues from ovalbumin-challenged mice.

Our present findings showed that artesunate prevented inflammatory cell infiltration into the airways as shown by a significant drop in total cell counts and eosinophil and lymphocyte counts in BAL fluid, and in tissue eosinophilia in lung sections. Eosinophils is considered to play a central role in the pathogenesis of allergic inflammation. Leukocyte transmigration into the airways is orchestrated by cytokines like IL-4, IL-5 and IL-13, and coordinated by specific chemokines like eotaxin and RANTES in combination with adhesion molecules such as intercellular adhesion molecule-1 (ICAM-1), vascular cell adhesion molecule-1 (VCAM-1) and Eselectin (7, 33). Cytokine receptor activation by IL-4, IL-5 and IL-13 induces PI3K/Akt signaling cascade (46, 47), and IL-4 and IL-13 are potent inducers of eotaxin and RANTES expression in human bronchial epithelial cells (48). PI3Kγ plays an imperative role in mediating eotaxin-induced eosinophil chemotaxis in vitro (18). Inhibition of class IA PI3K in eosinophil has been shown to block IL-5-induced β2-integrin adhesion of human eosinophils to ICAM-1 (47). Furthermore, selective PI3Kβ inhibition in mice suppressed aeroallergen-induced VCAM-1 and ICAM-1 expression in lungs (42). Accordingly, we have demonstrated that artesunate strongly suppressed ICAM-1, VCAM-1 and E-selectin mRNA expression and eotaxin production in OVA-challenged lungs, and IL-8, RANTES and MCP-1 mRNA expression in EGF-stimulated normal human bronchial epithelial cells. Taken together, the observed reduction in airway eosinophilia by artesuante may be a result of combined inhibitory effects on IL-4, IL-5, IL-13, eotaxin and RANTES production, and on adhesion molecule expression, secondary to inhibition of PI3K/Akt pathway. In addition, expression of eotaxin, RANTES, ICAM-1, CAM-1 and E-selectin are NF—KB-dependent (49), and their down-regulation may also be due to artesunate-mediated inhibition of NF-κB transactivation.

Figure 4:
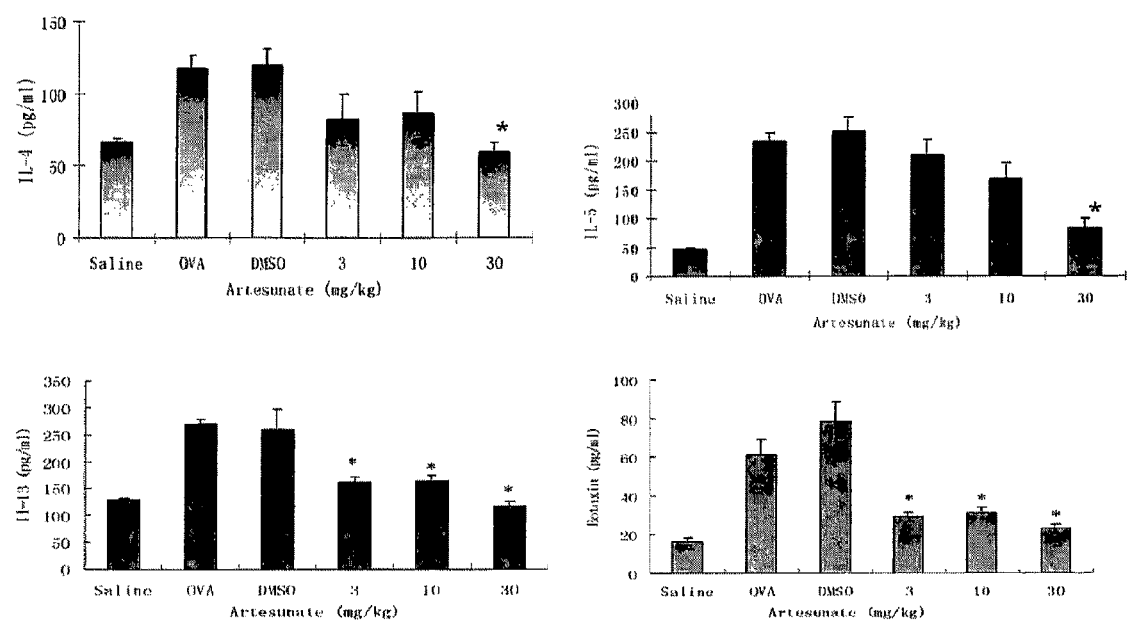
FIG. 4: Effects of artesunate on cytokine and chemokine level in BALF. BAL fluids were collected 24 hours after the last OVA aerosol challenge. Level of IL-4, IL-5, IL-13 and eotaxin were analysed using enzyme-linked immunosorbant assay (ELISA).
Figure 5:
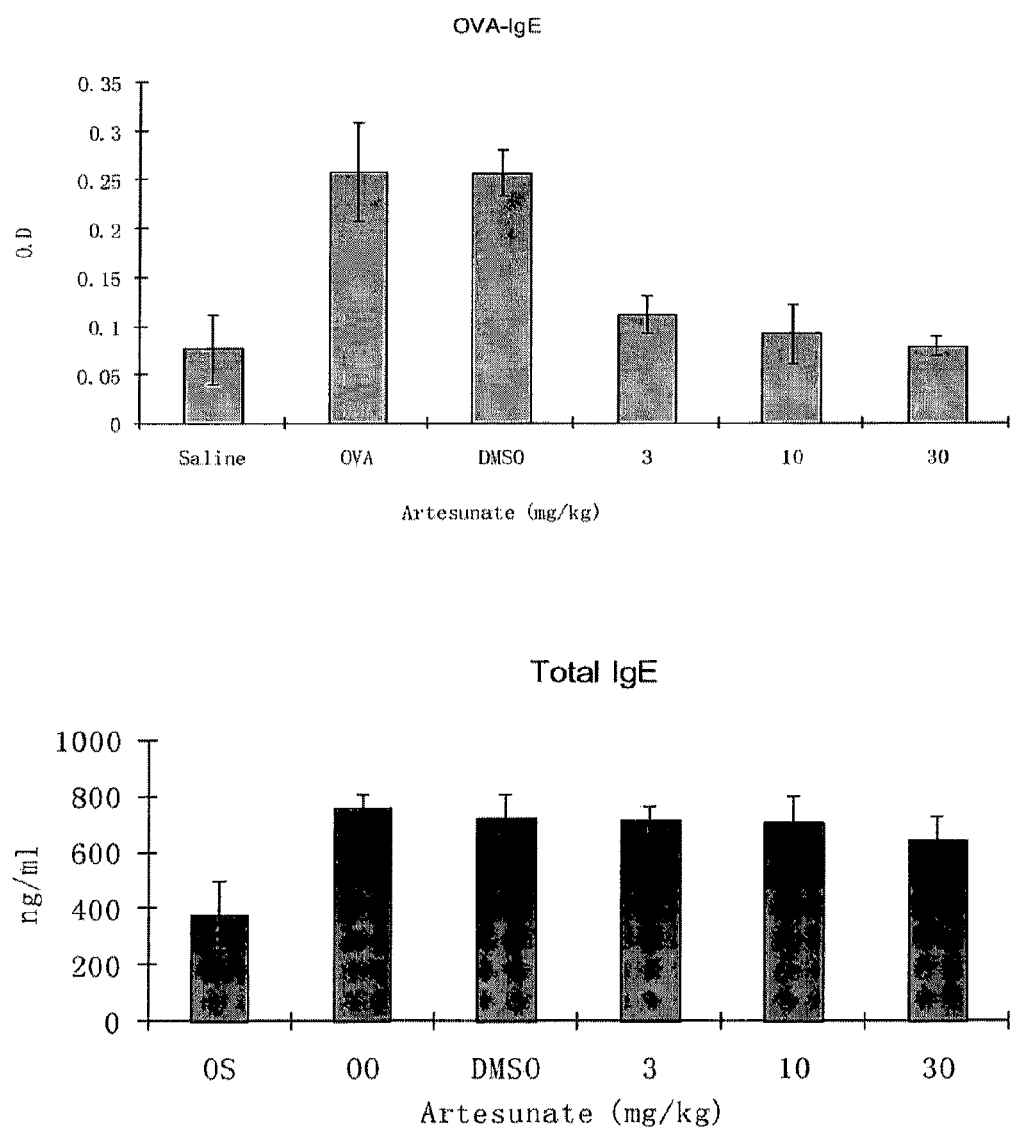
FIG. 5: Effects of artesunate on serum IgE production. Mouse serum was collected 24 hours after the last OVA aerosol challenge. The levels of OVA-specific IgE and total IgE were analysed using ELISA. Artesunate significantly lowered OVA-specific IgE levels, but had no effect on the levels of total IgE, indicating an OVA-specific inhibition on the Th2 response by artesunate.
Figure 6:
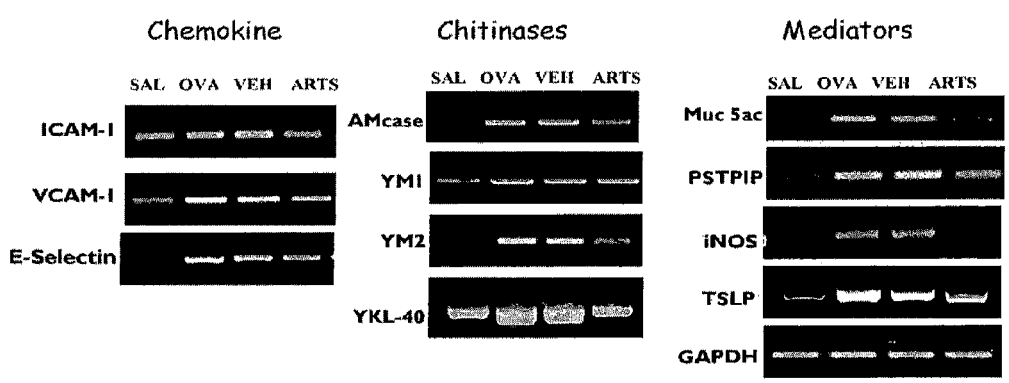
FIG. 6: Effects of artesunate on pulmonary mRNA expression of inflammatory markers. Lung tissues were collected 24 hours after the last OVA aerosol challenge. Total mRNA was extracted using TriZol reagent and the PCR product were separated in a 2% agarose gel visualized under UV light. GAPDH was used as an internal control.

In addition, artesunate was able to suppress ovalbumin-induced cytokine production obtained from BAL fluid (FIG. 4) and serum IgE levels (FIG. 5). Furthermore, artesunate was able to suppress ovalbumin-induced expression pro-inflammatory adhesion molecules and biomarkers (FIG. 6).

We have also demonstrated a dramatic reduction in airway mucus production in artesunate-treated mice as compared with DMSO control. Cumulative evidence indicates that IL-4, IL-5, IL-6, IL-13, IL-17 and IL-33 induce goblet cell hyperplasia and mucin production in mice. Mice deficient in p110δ or p110γ PI3K had impaired mucus production in response to aeroallergen challenge (21, 22). Muc5ac gene expression is also dependent on the transcriptional activity of NF-κB (49). We observed a substantial drop in Muc5ac mRNA expression by artesunate in OVA-challenged lungs. As such, the marked decrease in mucus production in the lungs of artesunate-treated mice may be attributable to a significant reduction of Th2 cytokine levels, together with inhibition of NF-κB transactivation in airway epithelium.

Elevated serum IgE levels are a hallmark of the Th2 immune response. Our data showed that serum levels of OVA-specific IgE were substantially reduced by artesunate in OVA-challenged mice. Similarly, PI3K plays a crucial role in B cell proliferation and development, and IL-4 and IL-13 are important in directing B cell growth, differentiation and secretion of IgE. The biological activities of IgE are mediated through its interaction with the FcεRI on mast cells and basophils. PI3Kδ is critical for FcεRI activation-induced mast cell degranulation and cytokine production (i.e. IL-6 and TNF-α) (20, 50). Akt has been shown to regulate NF-κB transcriptional activity in bone marrow-derived mast cells and cytokine production (51). Therefore, the observed reduction in serum OVAspecific IgE by artesunate may be contributed to by its inhibitory effect on B cell activation via inhibition of PI3K/Akt signaling pathway, and on IL-4- and IL-13-mediated class switching to IgE.

A family of chitinase proteins including AMCase, Yml, Ym2 and YKL-40 has recently been found to be markedly elevated in allergic airway inflammation in human and in mouse asthma models (30-32). AMCase level is increased in a mouse asthma model and in asthmatic subjects. When given intratracheally, IL-13 elevates Ym1 and Ym2 levels in BAL fluid from mice in vivo (52). Besides, YKL-40 serum level correlates positively with asthma severity, airway remodeling and deterioration of pulmonary function in asthmatic subjects (32). Overall, chitinases may play a role in airway inflammation and remodeling. Our data show that artesunate markedly down-regulated AMCase, Ym2 and YKL-40 mRNA expression in the lungs of OVA-challenged mice. These may be a consequence of the major drop in IL-4 and IL-13 levels in the airways with artesunate treatment and may contribute to the diminished pulmonary eosinophilia.

Patients with bronchial asthma produce higher level of exhaled nitrogen monoxide (NO) as compared with healthy controls, and the NO level may reflect the severity of asthma. It appears that increased exhaled NO is associated with increased iNOS expression in the lung epithelium of asthma patients (54). IL-13 has been shown to induce iNOS expression in normal human bronchial epithelial cells leading to elevated NO production (26). Class IA PI3K plays an important role in the dimerization of iNOS for the NO production (55). In addition, iNOS gene expression is regulated by the NF-κB transcriptional activity (49). Our results show that artesunate markedly suppressed the OVA-induced iNOS expression in the lungs, which may be due to inhibition of PI3K/Akt pathway and of the downstream NF-κB activity, and the reduced level of IL-13 in the allergic airways.

It is believed that inflammatory mediators released during the allergic inflammation play a critical role in AHR development (8). Besides, activation of PI3K/Akt and its downstream molecules tuberin, p70S6K and 4E-BP1 leads to airway smooth muscle hypertrophy and hyperplasia (56, 57). More recently, p110δ PI3K has been shown to mediate IL-13-induced mouse tracheal smooth muscle hyperreactivity to methacholine (58). We report here that artesunate significantly inhibited OVA-induced AHR to increasing concentrations of methacholine. Thus, the observed reduction of AHR by artesunate may be associated with the reduction in Th2 cytokine production, tissue eosinophilia, serum IgE level and airway smooth muscle contractile machinery via inhibition of PI3K/Akt signaling pathway.

Animals

Female BALB/c mice, 6 to 8 weeks old (Interfauna, East Yorkshire, UK), were sensitized and challenged with OVA as described (24). Artesunate (3, 10, and 30 mg/kg; Sigma, St. Louis, Mo.) or vehicle (6% dimethyl sulfoxide [DMSO]) in 0.1 ml saline was given by intraperitoneal injections 2 hours before each OVA aerosol challenge. Saline aerosol was used as a negative control. Animal experiments were performed according to the Institutional guidelines for Animal Care and Use Committee of the National University of Singapore.

Bronchoalveolar Lavage Fluid and Serum Analysis

Mice were anesthetized 24 hours after the last aerosol challenge and bronchoalveolar lavage (BAL) was performed as described (24). BAL fluid total and differential cell counts, and cytokine and chemokine levels were determined as described (24). Blood was collected by cardiac puncture, and serum levels of total IgE and OVA-specific IgE, IgG1, and IgG2a levels were determined as described (24).

Histologic Analysis

Lungs were fixed in 10% neutral formalin, paraffinized, cut into 5-μm sections, and stained with hematoxylin and eosin (H&E) for examining cell infiltration and with periodic acid-Schiff stain (PAS) for measuring mucus production. Quantitative analysis was performed blinded as described (24).

Quantitative analyses of inflammatory cell infiltration and mucus production in lung sections were performed as previously described (24). Briefly, to determine the severity of inflammatory cell infiltration, peribronchial cell counts were performed blind based on a 5-point scoring system: 0, no cells; 1, a few cells; 2, a ring of cells a cell layer deep; 3, a ring of cells 2-4 cells deep; 4, a ring of cells of >4 cells deep. To determine the extent of mucus production, goblet cell hyperplasia in the airway epithelium was quantified blind using a 5-point grading system: 0, no goblet cells; 1, <25%; 2, 25-50%; 3, 50-75%; 4, >75%.

Measurements of AHR

Mice were anesthetized and tracheotomy was performed as described (24). The trachea was intubated with a cannula that was connected to the pneumotach, ventilator and nebulizer. Airway resistance (RI) and dynamic compliance (Cdyn) in response to increasing concentrations of nebulized mechacholine (0.5-8.0 mg/ml) were recorded using a whole-body plethysmograph chamber (Buxco, Sharon, Conn.) as described (24). Results are expressed as a percentage of the respective basal values in response to phosphate-buffered saline (PBS).

Cell Cultures

To determine the effects of artesunate on OVA-specific immune responses in lymphocytes, thoracic lymph node cells were prepared as described (24). Cells were exposed to 200 μg/μl OVA for 72 hours. Concanavalin A (Con A, 10 μg/ml) was used as a positive control. Supernatants from parallel triplicate cultures were analyzed for cytokine levels by ELISA. Normal human bronchial epithelial cells were cultured in optimized bronchial epithelial bulletkit medium with supplements (Lonza, Basel, Switzerland). Cells were pretreated with 10 μM artesunate or vehicle (0.01% DMSO) 4 hours before stimulation with 100 μg/ml epidermal growth factor (EGF). Total and nuclear proteins, and mRNA were extracted from cells at specified time intervals.

Immunoblotting, mRNA Expression and NF-κB DNA-binding

Lung and cell culture protein lysates (10 mg per lane) were separated by 10% SDS-PAGE and immunoblots were developed as described (24). Immunoblots were probed with anti-Akt, anti-phospho-Akt (Ser$_{473}$), anti-tuberin, anti-phospho-tuberin (Ser$_{1462}$), anti-p70S6K, anti-phospho-p70S6K (Ser$_{389}$), anti-4E-BP1, anti phospho-4E-BP1 (Ser$_{65}$), and anti-β-actin antibodies (Cell Signaling Technology, Beverly, Mass.). Proteins were separated by 10% SDSPAGE, probed with anti-Akt, anti-phospho-Akt (Ser473), anti-tuberin, antiphospho-tuberin (Ser1462), anti-p 70S6K, anti-phospho-p70S6K (Ser389), anti-4EBP1, and anti-phospho-4E-BP1 (Ser65), and developed by enhanced chemiluminescence reagent. β-actin was used as an internal control. The experiments were repeated for three times. Primers for inflammatory genes are shown in Table 1 and mRNA expression was analyzed as described (24). Nuclear proteins were analyzed for NF-κB DNA-binding activity using TransAM NF-κB transcription factor assay kit (Active Motif, Carlsbad, Calif.). Total mRNA was extracted using TriZol reagent and the PCR products were separated in a 2% agarose gel visualized under UV light. β-actin was used as an internal control. The experiments were repeated for three times

TABLE 1

PRIMER SETS FOR REVERSE TRANSCRIPTASE-POLYMERASE CHAIN REACTION ANALYSIS

| Targets | Sequences | |
|---|---|---|
| | Forward | Reverse |
| m AMCase | 5'-TGGGTTCTGGGCCTACTATG-3' | 5'-GCTTGACAATGCTGCTGGTA-3' |
| m Ym2 | 5'-CAGAACCGTCAGACATTCATTA-3' | 5'-ATGGTCCTTCCAGTAGGTAATA-3' |
| m YKL-40 | 5'-GTACAAGCTGGTCTGCTACT-3' | 5'-GTTGGAGGCAATCTCGGAAA-3' |
| m ICAM-1 | 5'-CATCGGGGTGGTGAAGTCTGT-3' | 5'-TGTGGGGGAAGTGTGGTC-3' |
| m VCAM-1 | 5'-CAAGGGTGACCAGCTCATGAA-3' | 5'-TGTGCAGCCACCTGAGATCC-3' |
| m E-selectin | 5'-AACGCCAGAACAACAATTCC-3' | 5'-TGAATTGCCACCAGATGTGT-3' |
| m Muc5ac | 5'-GAGTGACATTGCAGGAAGCA-3' | 5'-CAGAGGACAGGAAGGTGAGC-3' |
| m iNOS | 5'-GTCAACTGCAAGAGAACGGAGAC-3' | 5'-GAGCTCCTCCAGACGGGTAGGCTTG-3' |
| m TSLP | 5'-CGACAGCATGGTTCTTCTCA-3' | 5'-CGACAGCATGGTTCTTCTCA-3' |
| m IL-17A | 5'-CCGCAATGAAGACCCTGATAGA-3' | 5'-CAGCATCTTCTCGACCCTGAAA-3' |
| m IL-33 | 5'-GATGGGAAGAAGGTGATGGGTG-3' | 5'-TTGTGAAGGACGAAGAAGGC-3' |

TABLE 1-continued

PRIMER SETS FOR REVERSE TRANSCRIPTASE-POLYMERASE CHAIN REACTION ANALYSIS

| Targets | Sequences | |
|---|---|---|
| | Forward | Reverse |
| h IL-6 | 5'-CAGGAGAAGATTCCAAAGAT-3' | 5'-ACTGGTTCTGTGCCTGCAGC-3' |
| h IL-8 | 5'-ATGACTTCCAAGCTGGCCGTGGCT-3' | 5'-TCTCAGCCCTCTTCAAAAACTTCTC-3' |
| h RANTES | 5'-ATGAAGGTCTCCGCGGCACGCCT-3' | 5'-CTAGCTCATCTCCAAAGAGTTG-3' |
| h MCP-1 | 5'-GATCTCAGTGCAGAGGCTCG-3' | 5'-TGCTTGTCCAGGTGGTCCAT-3' |
| h/m β-Actin | 5'-TCATGAAGTGTGACGTTGACATCCGT-3' | 5'-CCTAGAAGCATTTGCGGTGCACGATG-3' |

Statistical Analysis

Data are presented as means±SEM. One-way ANOVA followed by Dunnett's test was used to determine significant differences between treatment groups. Significant levels were set at P<0.05.

RESULTS

Figure 7:
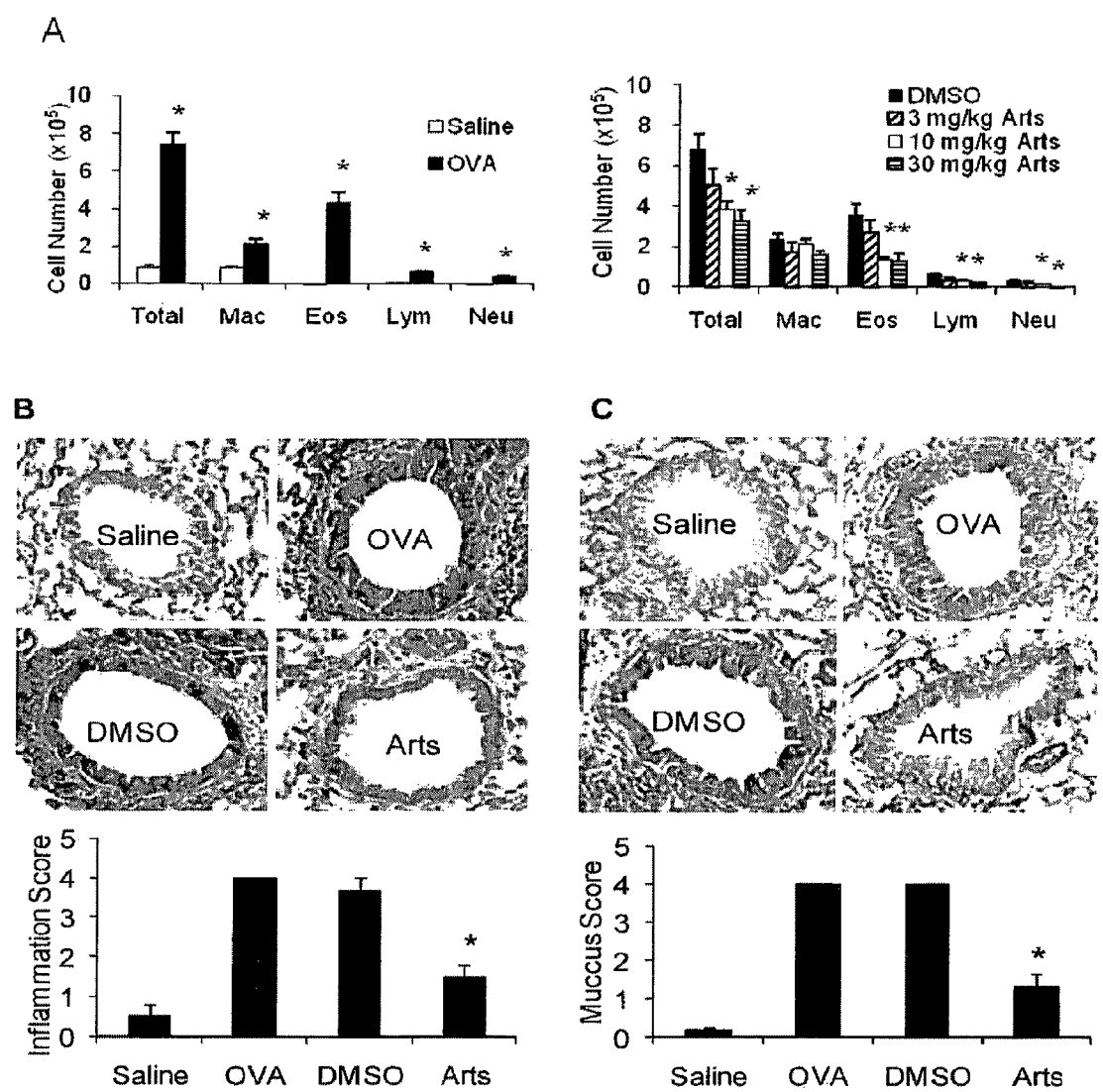
FIG. 7. Effects of artesunate on OVA-induced inflammatory cell recruitment and mucus hypersecretion. (A) Inflammatory cell counts in BAL fluid obtained from sensitized mice 24 hours after the last saline aerosol (n=6 mice per group) or OVA aerosol (n=7 mice per group) challenge. Artesunate dose-dependently reduced OVA-induced inflammatory cell counts in BAL fluid from sensitized mice 24 hours after the last OVA aerosol challenge (DMSO, n=7; 0.1 mg/kg, n=7; 0.5 mg/kg, n=10; and 1 mg/kg, n=9 mice per group). Differential cell counts were performed on a minimum of 500 cells to identify eosinophil (Eos), macrophage (Mac), neutrophil (Neu), and lymphocyte (Lym). Histological examination of lung tissue eosinophilia (B, magnification ×200) and mucus secretion (C, magnification ×200) 24 hours after the last challenge of saline aerosol, OVA aerosol, OVA aerosol plus DMSO, or OVA aerosol plus 1 mg/kg andrographolide. Scoring of inflammatory cells and goblet cells was performed in at least 3 different fields for each lung section. Mean scores were obtained from 4 animals. *Significant difference from DMSO control, P<0.05.

Artesunate Suppresses OVA-Induced Inflammatory Cell Recruitment and Mucus Production BAL fluid was collected 24 hours after the last OVA or saline aerosol challenge, and total and differential cell counts were performed. OVA inhalation markedly increased total cell and eosinophil counts, and slightly yet significantly (P<0.05) increased macrophage, lymphocyte and neutrophil counts, as compared with saline aerosol control. Artesunate (3, 10 and 30 mg/kg) drastically decreased the total cell and eosinophil counts in BAL fluid in a dose-dependent manner as compared with the DMSO vehicle control (FIG. 7A). We have conducted flow cytometric analysis of peripheral blood leukocytes obtained from saline challenged, OVA-challenged, vehicle control, and artesunate-treated mice. Similar percentages of CD3+, CD4+, CD8+ T cells, B cells (B220), NK cells (NK 1.1), neutrophils and monocytes were observed in all mice (data not shown). Hence, artesunate-induced reduction of eosinophil and lymphocyte pulmonary recruitment is unlikely due to any potential nonspecific cytotoxic effects of the drug.

Lung tissue was also collected 24 hours after the last OVA or saline aerosol challenge. OVA aerosol challenge induced marked infiltration of inflammatory cells into the peribronchiolar and perivascular connective tissues as compared with saline aerosol challenge. Artesunate (30 mg/kg) markedly diminished the eosinophil-rich leukocyte infiltration as compared with DMSO control (FIG. 7B). On the other hand, OVA-challenged mice, but not saline-challenged mice, developed marked goblet cell hyperplasia and mucus hypersecretion in the bronchi. OVA-induced mucus hypersecretion was significantly halted by artesunate (30 mg/kg) (FIG. 7C).

Figure 8:
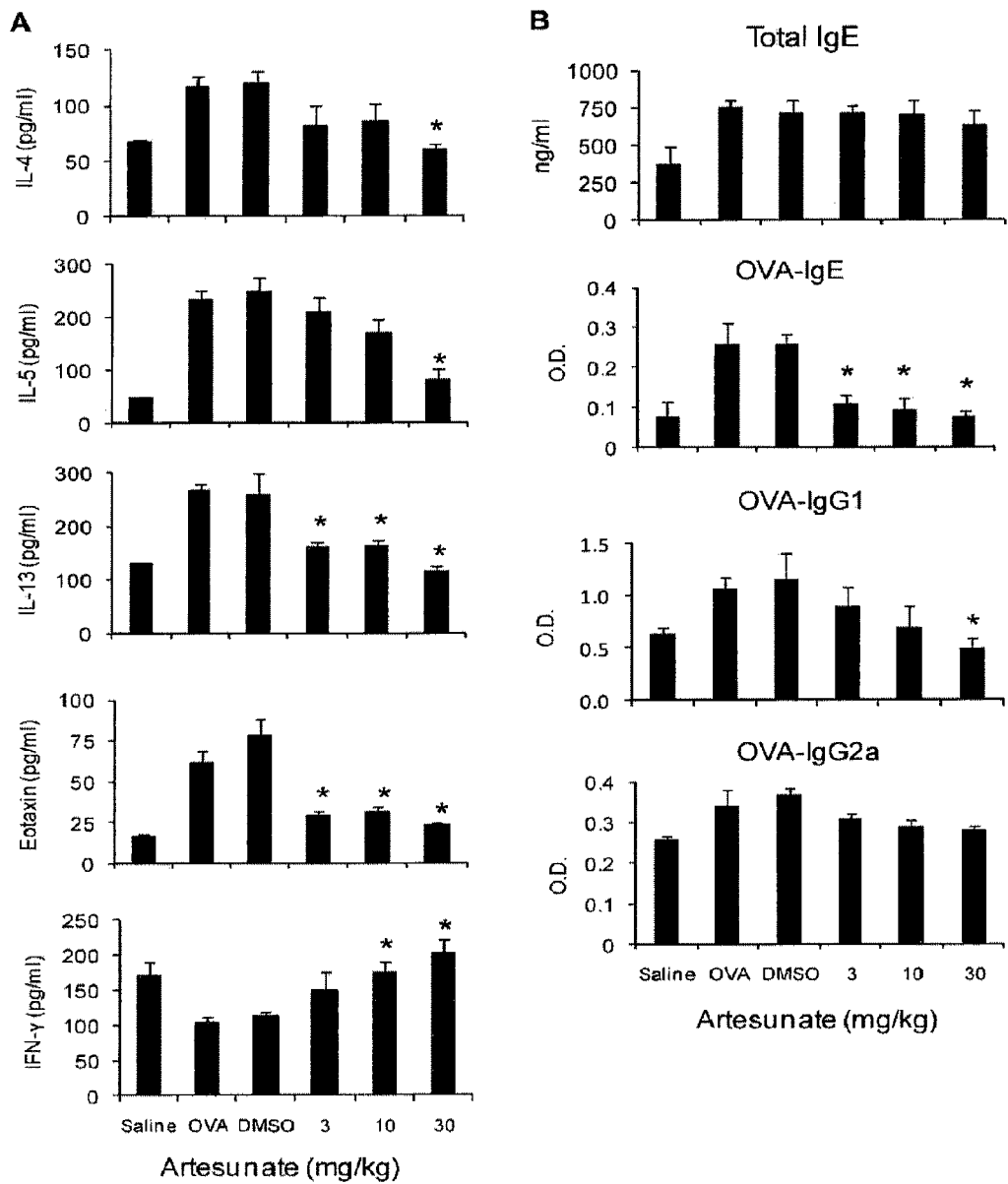
FIG. 8. Effects of artesunate on OVA-induced BAL fluid cytokine and chemokine levels and serum Ig production. (A) BAL fluids were collected 24 hours after the last OVA aerosol challenge. Levels of IL-4, IL-5, IL-13, eotaxin and IFN-γ were analyzed using ELISA (n=6-9 mice per group). Lower limits of detection were as follows: IL-1 and IL-5 at 4 pg/ml; IL-13 and IFN-γ at 15.6 pg/ml; and eotaxin at 2 pg/ml. (B) Mouse serum was collected 24 hours after the last OVA aerosol challenge. The levels of total IgE, OVA-specific IgE, OVA-specific IgG1, and OVA-specific IgG2a were analyzed using ELISA (n=6-9 mice per group). Values shown are the mean±SEM. *Significant difference from DMSO control, P<0.05.

Artesunate Reduces OVA-Induced BAL Fluid Th2 Cytokine Levels and Serum Ig Production OVA inhalation in sensitized mice caused a notable increase in IL-4, IL-5, IL-13 and eotaxin levels in BAL fluid as compared with saline aerosol control (FIG. 8A). In contrast, BAL fluid level of IFN-γ, a Th1 cytokine, dropped slightly in OVA challenged mice. Artesunate drastically reduced IL-13 and eoxtain, and to a lesser extent, IL-4 and IL-5 levels in BAL fluid in a dose-dependent manner as compared with DMSO control (FIG. 8A). Noticeably, artesunate at 10 and 30 mg/kg up-regulated IFN-γ level in BAL fluid. This finding may imply that artesuante is able to modify the Th2-predominant immune activity in our OVA-induced mouse asthma model.

To further evaluate whether artesunate could modify an ongoing OVA-specific Th2 response in vivo, serum levels of total IgE, and OVA-specific IgE, IgG1 and IgG2a were determined using ELISA. Marked elevation in serum total IgE, OVAspecific IgE and IgG1 levels, but not OVA-specific IgG2a level, were observed in OVA-challenged mice as compared with saline-challenged mice (FIG. 8B). Artesunate strongly suppressed OVA-specific IgE levels even at the lowest dose (3 mg/kg), and, to a lesser extent, the serum level of OVA-specific IgG1 with significant effects at higher dose (FIG. 8B). Artesunate had no effects on the serum level of OVA-specific IgG2a, indicating a specific inhibition of the Th2 response by artesunate.

Artesunate Suppresses OVA-Specific Lymphocyte Responses In Vitro

Figure 9:
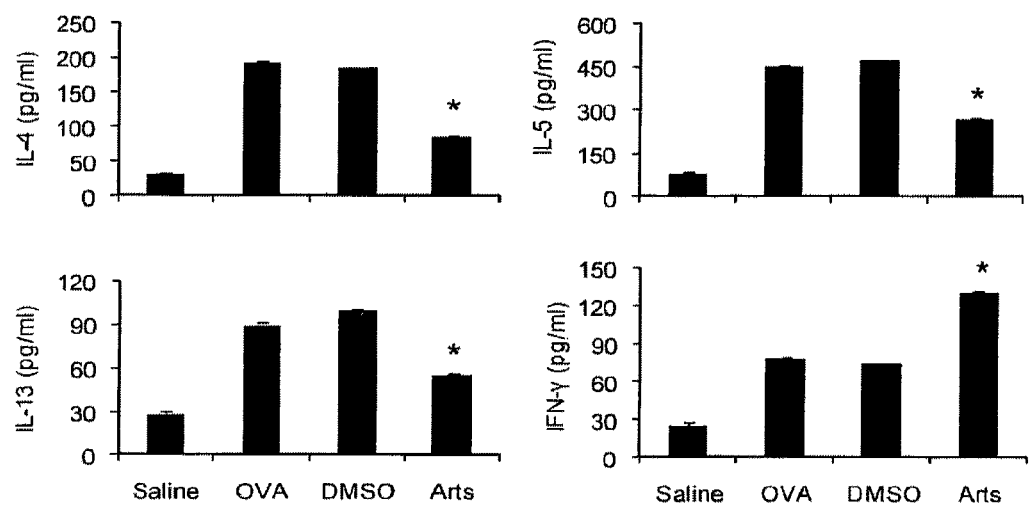
FIG. 9. Effects of artesunate on OVA-specific response in vitro. Thoracic lymph nodes cells (n=4 mice per group) were harvested from mice 24 hours after the last OVA or saline aerosol challenge, and cultured for 72 hours with medium alone or OVA (200 μg/ml). The levels of IL-4, IL-5, and IFN-γ in culture supernatant were determined using ELISA. Values shown are the mean±SEM of triplicate cultures of pooled lymph node cell suspensions. *Significant difference from DMSO control, P<0.05.

To assess whether artesunate treatment could directly influence lymphocyte function, we examined OVA-specific immune responses in thoracic lymph node cultures. The in vitro OVA-specific production of IL-4, IL-5 and IL-13 was markedly higher in lymphocytes isolated from OVA-challenged mice than those from saline-challenged mice (FIG. 9). Artesunate (30 mg/kg) pretreatment significantly (P<0.05) lowered the levels of IL-4, IL-5 and IL-13. In contrast, in vitro OVA-specific IFN-γ production was found to be elevated in mice treated with artesunate (30 mg/kg). The observed immune modulation by artesunate in vitro was OVA-specific because Con A-induced production of IL-4, IL-5, IL-13 and IFN-γ in parallel cultures was not affected (data not shown).

Artesunate Reduces OVA-Induced AHR in Mice

Figure 10:
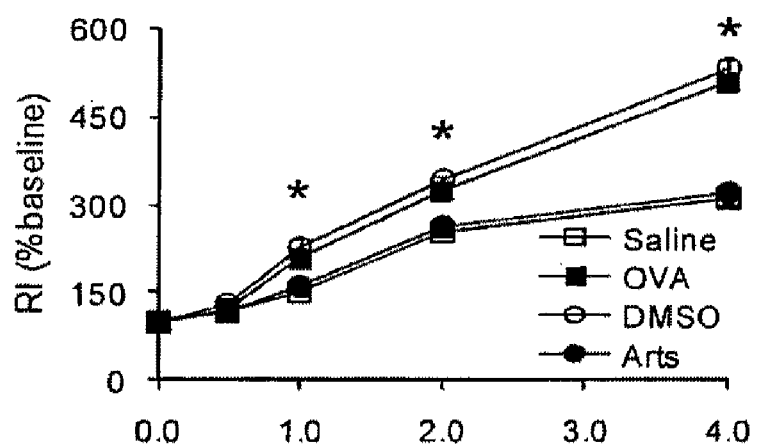
FIG. 10. Effects of artesunate on OVA-induced AHR. Airway responsiveness of mechanically ventilated mice in response to aerosolized methacholine was measured 24 hours after the last saline aerosol or OVA aerosol with pretreatment of either DMSO or 30 mg/kg artesunate. AHR is expressed as percentage change from the baseline level of (A) lung resistance (R1, n=6 mice per treatment group) and (B) dynamic compliance (Cdyn, n=6 mice per treatment group). R1 is defined as the pressure driving respiration divided by flow. Cdyn refers to the distensibility of the lung and is defined as the change in volume of the lung produced by a change in pressure across the lung. *Significant difference from DMSO control, P<0.05.
Figure 10:
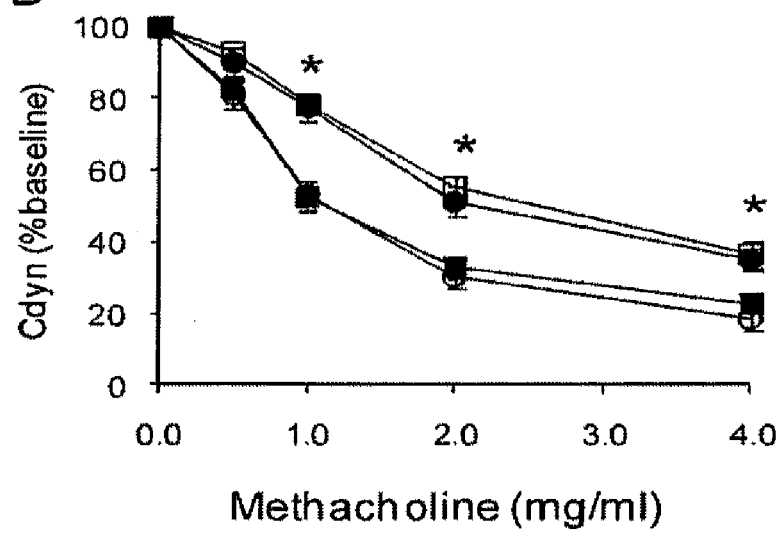

To investigate the effect of artesunate on AHR in response to increasing concentrations of methacholine, we measured both RI and Cdyn in mechanically ventilated mice. RI is defined as the pressure driving respiration divided by flow. Cdyn refers to the dispensability of the lung and is defined as the change in volume of the lung produced by a change in pressure across the lung. OVA challenged mice developed AHR which is typically reflected by high RI and low Cdyn (FIG. 10). Artesunate (30 mg/kg) dramatically reduced RI and restored Cdyn in OVA-challenged mice in response to methacholine aerosol, suggesting that immune-mediated airway pathology in vivo was modified.

Figure 11:
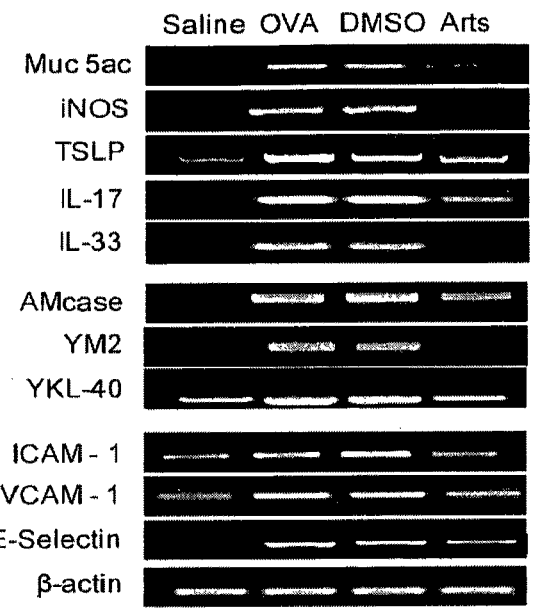
FIG. 11. Effects of artesuante on OVA-induced inflammatory gene expression, PI3K/Akt activation and NF-κB DNA-binding activity in allergic airway inflammation. (A) Lung tissues were collected 24 hours after the last OVA aerosol challenge. Total mRNA was extracted and separated on an agarose gel and visualized as described (n=3 mice per group). (B) Immunoblotting of Akt, tuberin, p70S6K and 4E-BP1 in protein extracts of lung tissues isolated from mice 24 hours after the last saline aerosol or OVA aerosol challenge pretreated with either DMSO or 30 mg/kg artesunate. (n=3 mice per group). (C) Nuclear p65 DNA-binding activity was determined using a TRANSAM™ p65 transcription factor ELISA kit. Values shown are the mean± SEM of four separate experiments. *Significant difference from DMSO control, P<0.05.
Figure 11:
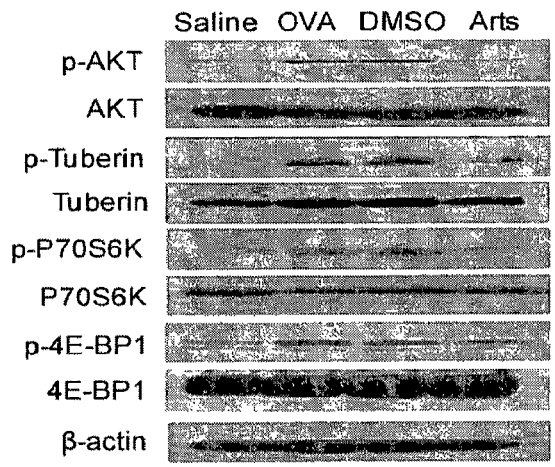
Figure 11:
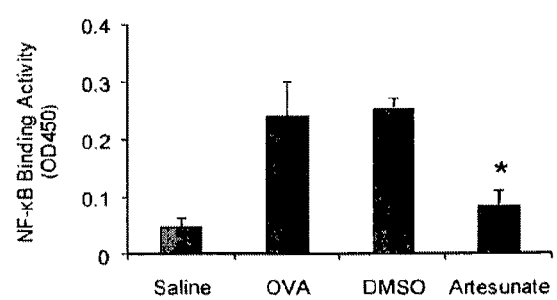

Artesunate Inhibits OVA-Induced Inflammatory Gene Expression and PI3K/Akt Activation in Allergic Airway Inflammation OVA aerosol challenge markedly up-regulated lung mRNA level of Muc5ac, which is essential for mucus hypersecretion (25); inducible nitric oxide synthase (iNOS), the enzyme responsible for nitric oxide (NO) production in allergic airway inflammation (26); thymic stromal lymphopoietin (TSLP), a cytokine key to the initiation of Th2 immune response (27); IL-17 and IL-33, two effector cytokines that have recently been shown essential for airway inflammation and remodeling (28, 29); of chitinase family members including acidic mammalian chitinase (AMCase), Ym2 and YKL-40, which have recently been shown to play critical roles in airway inflammation and remodeling (30-32); and of adhesion molecules such as ICAM-1, VCAM-1 and E-selectin, which are pivotal for pulmonary recruitment of inflammatory cells like eosinophils and lymphoctyes (7, 33). Pretreatment with artesunate (30 mg/kg) demonstrated strong suppression of Muc5ac, iNOS, TSLP, IL-17, IL-33, AMCase, Ym-2, YKL-40, ICAM-1, VCAM-1 and E-selectin, in the allergic airways (FIG. 11A).

To verify that the anti-inflammatory mechanism of action by artesunate in OVA challenged mice was mediated through the inhibition of the PI3K/Akt signaling pathway, we examined the phosphorylation cascade of Akt, tuberin, p70 ribosomal S6 kinase (p70S6K) and eukaryotic initiation factor 4E-binding protein 1 (4E-BP1) in lung tissues obtained 24 hours after the last OVA or saline aerosol challenge. OVA challenge markedly raised the phosphorylation state of Akt (ser$_{473}$), tuberin(thr$_{1462}$), p70S6K(thr$_{389}$) and 4E-BP1(ser$_{65}$) as compared with saline aerosol control (FIG. 11B). Artesunate (30 mg/kg) markedly reduced the phsophorylation of Akt, tuberin, p70S6K and 4E-BP1 to the basal levels. Besides, PI3K/Akt pathway activation has been shown to promote NF-κB DNA binding activity (34). Artesunate significantly suppressed OVA-induced NF-κB transactivation in lung tissues to basal level (FIG. 11C). Our findings suggest that artesunate may exert its anti-inflammatory actions via inhibition of PI3K/Akt pathway.

Figure 12:
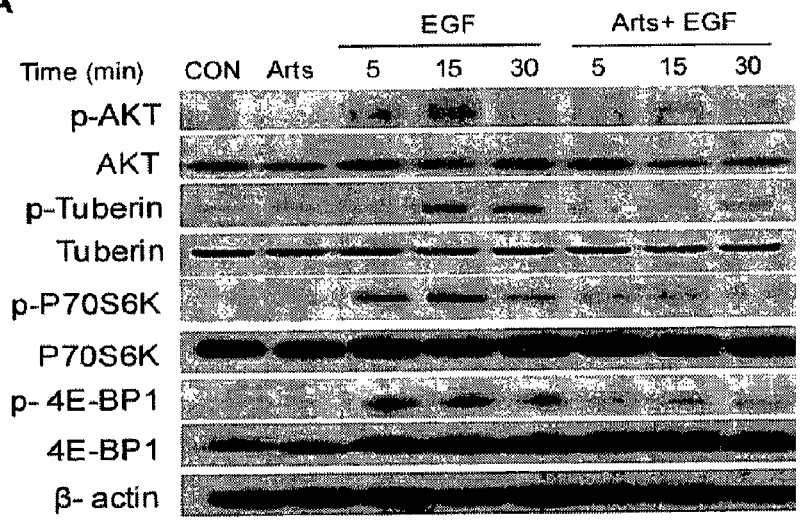
FIG. 12. Effects of artesuante on EGF stimulation of normal human bronchial epithelial cells. (A) Epithelial cells were stimulated with 100 ng/ml EGF in the presence and absence of 10 μM artesunate for 5, 15 and 30 minutes before total proteins were extracted for subsequent immunoblotting analysis. Immunoblots were probed with anti-Akt, anti-phospho-Akt (Ser473), anti-tuberin, anti-phospho-tuberin (Ser1462), anti-p70S6K, anti-phospho-p70S6K (Ser389), anti-4E-BP1, anti-phospho-4E-BP1 (Ser65) or anti-γ-actin antibody, and developed by enhanced chemiluminescence reagent. γ-actin was used as an internal control. (B) DNA-binding activity of p65 NF-κB in nuclear extracts of epithelial cells stimulated with EGF for 30 minutes in the presence and absence of 10 μM artesunate was determined using a TRANSAM™ p65 transcription factor ELISA kit. (C) Epithelial cells were stimulated with 100 ng/ml EGF in the presence and absence of 10 μM artesunate for 12 hours before total mRNA was extracted using TriZol reagent. PCR products were separated in a 2% agarose gel and visualized under UV light. γ-actin was used as an internal control. This is a representative gel from 4 separate experiments with similar pattern of results. Values shown are the mean±SEM of three separate experiments. *Significant difference from DMSO control, P<0.05.
Figure 12:
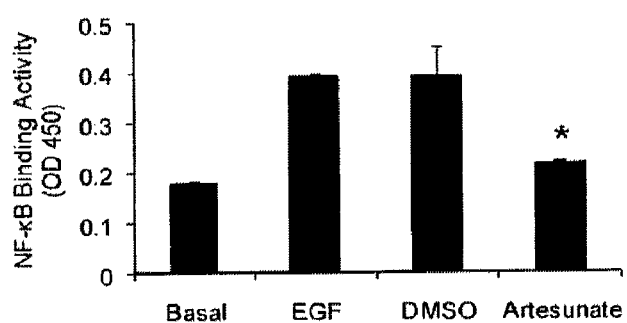
Figure 12:
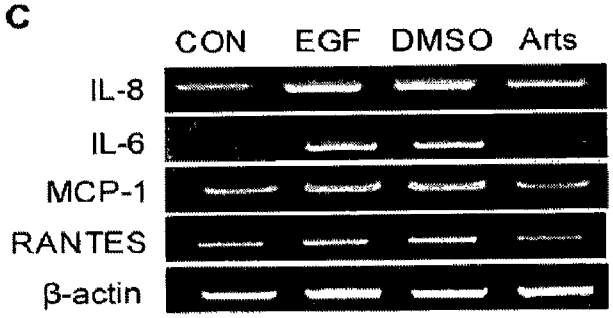

Artesunate Inhibits EGF-induced PI3K/Akt Activation in Primary Human Bronchial Epithelial Cells To further explore anti-inflammatory mechanisms of action of artesunate in a relevant human airway cell type, we studied the effects of artesunate on EGF induced activation of PI3K/Akt signaling pathway and cytokine mRNA expression in normal human bronchial epithelial cells. EGF plays a critical role in asthma (35, 36) and is a potent stimulator of human airway epithelial cells (37). EGF induced a rapid phosphorylation of Akt, tuberin, p70S6K and 4E-BP1 (FIG. 12A). This was accompanied with the up-regulation of NF-κB DNA binding activity (FIG. 12B). Artesunate markedly inhibited the EGF-induced phosphorylation of Akt, tuberin, p70S6K and 4E-BP1, and NF-κB transactivation. Furthermore, artesunate noticeably blocked EGF-induced up-regulation of IL-6, IL-8, monocyte chemoattractant protein-1 (MCP-1) and RANTES mRNA expression in normal human bronchial epithelial cells (FIG. 12C).

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

While the invention has been described with reference to specific methods and embodiments, it will be appreciated that various modifications and changes may be made without departing from the invention.

REFERENCES

1. Galli S J, Tsai M, Piliponsky A M. The development of allergic inflammation. *Nature* 2008; 454: 445-454.
2. Medoff B D, Thomas S Y, Luster A D. T cell trafficking in allergic asthma: the ins and outs. *Annu Rev Immunol* 2008; 26: 205-232.
3. Li-Weber M, Krammer P H. Regulation of IL4 gene expression by T cells and therapeutic perspectives. *Nat Rev Immunol* 2003; 3: 534-543.
4. Galli S J, Grimbaldeston M, Tsai M. Immunomodulatory mast cells: negative, as well as positive, regulators of immunity. *Nat Rev Immunol* 2008; 8: 478-486.
5. Takatsu K, Nakajima H. IL-5 and eosinophilia. *Curr Opin Immunol* 2008; 20: 288-294.

6. Wills-Karp M. Interleukin-13 in asthma pathogenesis. *Immunol Rev* 2004; 202: 175-190.
7. Hogan S P, Rosenberg H F, Moqbel R, Phipps S, Foster P S, Lacy P, Kay A B, Rothenberg M E. Eosinophils: biological properties and role in health and disease. *Clin Exp Allergy* 2008; 38: 709-750.
8. Cockcroft D W, Davis B E. Mechanisms of airway hyperresponsiveness. *J Allergy Clin Immunol* 2006; 118: 551-559.
9. Woodrow C J, Haynes R K, Krishna S. Artemisinins. *Postgrad Med J* 2005; 81: 71-78.
10. Rosenthal P J. Artesunate for the treatment of severe falciparum malaria. *N Engl J Med* 2008; 358: 1829-1836.
11. Krishna S, Bustamante L, Haynes R K, Staines H M. Artemisinins: their growing importance in medicine. *Trend Pharmacol Sci* 2008; 29 :520-527.
12. Hou J, Wang D, Zhang R, Wang H. Experimental therapy of hepatoma with artemisinin and its derivatives: in vitro and in vivo activity, chemosensitization, and mechanisms of action. *Clin Cancer Res* 2008; 14: 5519-5530.
13. Efferth T, Romero M R, Wolf D G, Stamminger T, Marin J J G, Maarschall M. The antiviral activities of artemisinin and artesunate. *Clin Infect Dis* 2008; 47: 804-811.
14. Rabe K F, Hurd S, Anzueto A, et al. (2007). "Global Strategy for the Diagnosis, Management, and Prevention of Chronic Obstructive Pulmonary Disease: GOLD Executive Summary". *Am. J. Respir. Crit. Care Med.* 176 (6): 532-55.
15. Li W D, Dong Y J, Tu Y Y, Lin Z B. Dihydroarteannuin ameliorates lupus symptom of BXSB mice by inhibiting production of TNF-α and blocking the signaling pathway NF-κB translocation. *Int immunopharmacol* 2006; 6: 1243-1250.
16. Li B, Zhang R, Li J, Zhang L, Ding G, Luo P, He S, Dong Y, Jiang W, Lu Y, et al. Antimalarial artesunate protects sepsis model mice against heat-killed *Escherichia coli* challenge by decreasing TLR4, TLR9 mRNA expressions and transcription factor NF-κB activation. Int Immunopharmacol 2008; 8: 379-389.
17. Wang Z, Qiu J, Guo T B, Liu A, Wang Y, Li Y, Zhang J Z. Anti-inflammatory properties and regulatory mechanism of a novel derivative of artemisinin in experimental autoimmune encephalomyelitis. *J Immunol* 2007; 179: 5958-5965.
18. Thomas M, Edwards M J, sawicka E, Duggan N, Hirsch E, Wymann M P, Owen C, Trifilieff A, Walker C, Westwick J, Finan P. Essential role of phosphoinositide 3-kinase gamma in eosinophil chemotaxis within acute pulmonary inflammation. *Immunology* 2008; 126: 413-422.
19. Fruman D A, Bismuth G. Fine tuning the immune response with PI3K. *Immunol Rev* 2009; 228: 253-272.
20. Kim M S, Radinger M, Gilfillan A M. The multiple roles of phosphoinositide 3-kinase in mast cell biology. *Trends Immunol* 2008; 29: 493-501.
21. Nashed B F, Zhang T, Al-Alwan M, Srinivasan G, Halayko A J, Okkenhaug K, Vanhaesebroeck B, HayGlass K T, Marshall A J. Role of the phosphoinositide 3-kinase p110δ in generation of type 2 cytokine responses and allergic airway inflammation. *Eur J Immunol* 2007; 37: 416-424.
22. Takeda M, Ito W, Tanabe M, Ueki S, Kato H, Kihara J, Tanigai T, Chiba T, Yamaguchi K, Kayaba H, et al. Allergic airway hyperresponsiveness, inflammation, and remodeling do not develop in phosphoinositide3-kinaseγ-deficient mice. *J Allergy Clin Immunol* 2009; 123: 805-812.
23. Lim D H, Cho J Y, Song D J, Lee S Y, Miller M, Broide D H. PI3Kγ-deficient mice have reduced levels of allergen-induced eosinophilic inflammation and airway remodeling. *Am J Physiol Lung Cell Mol Physiol* 2009; 296: L210-L219.
24. Bao Z, Guan S, Cheng C, Wu S, Wong S H, Kemeny D M, Leung B P, Wong W S F. A novel anti-inflammatory role for andrographolide in asthma via inhibition of the nuclear factor-KB pathway. *Am J Respir Crit. Care Med* 2009; 179: 657-665.
25. Turner J, Jones C E. Regulation of mucin expression in respiratory diseases. *Biochem Soc Trans* 2009; 37: 877-881.
26. Suresh V, Mih J D, George S C. Measurement of IL-13-induced iNOS-derived gas phase nitric oxide in human bronchial epithelial cells. *Am J Respir Cell Mol Biol* 2007; 37: 97-104.
27. Zhou B, Comeau M R, De Smedt T, Liggitt H D. Dahl M E, Lewis D B, Gyarmati D, Aye T, Campbell D J, Ziegler S F. Thymic stromal lymphopoetin as a key initiator of allergic airway inflammation in mice. *Nat Immunol* 2005; 6: 1047-1053.
28. Wakashin H, Hirose K, Maezawa, Kagami S I, Suto A, Watanabe N, Saito Y, Hatano M, Tokuhisa T, Iwakura Y, et al. IL-23 and Th17 cells enhance Th2-cell-mediated eosinophilic airway inflammation in mice. *Am J Respir Crit care Med* 2008; 178: 1023-1032.
29. Kearlye J, buckland K F, Mathie S A, Lloyd C M. Resolution of allergic inflammation and airway hyperreactivity is dependent upon disruption of the T1/ST2-IL-33 pathway. *Am J Respir Crit Care Med* 2009; 179: 772-781.
30. Yang C J, Liu Y K, Liu C L, Shen C N, Kuo M L, Su C C, Tseng C P, Yen T C, Shen C R. Inhibition of acidic mammalian chitinase by RNA interference suppresses OVA-sensitized allergic asthma. *Hum Gene Ther* 2009; 20:1-10.
31. Zhao J, Zhu H, Wong C H, Leung K Y, Wong W S F. Increased lungkine and chitinase levels in allergic airway inflammation: a proteomics approach. *Proteomics* 2005; 5: 2799-2807.
32. Chupp G L, Lee C G, Jarjour N, Shim Y M, Holm C T, He S, Dziura J D, Reed J, Coyle A J, Kiener P, et al. A chitinase-like protein in the lung and circulation of patients with severe asthma. *N Engl J Med* 2007; 357: 2016-2027.
33. Kelly M, Hwang J M, Kubes P. Modulating leukocyte recruitment in inflammation. *J Allergy Clin Immunol* 2007; 120: 3-10.
34. Gustin J A, Ozes O N, Akca H, Pincheira R, Mayo L D, Li Q, Guzman J R, Korgaonkar C K, Donner D B. Cell type-specific expression of the IκB kinases determines the significance of phosphatidylinositol 3-kinase/Akt signaling to NF-□B activation. *J Biol Chem* 2004; 279: 1615-1620.
35. Burgel P R, Nadel J A. Epidermal growth factor receptor-mediated innate immune responses and their roles in airway diseases. *Eur Respir J* 2008; 32: 1068-1081.
36. Tamaoka M, Hassan M, McGovern. T, Ramos-Barbon D, Jo T, Yoshizawa Y, Tolloczko B, Hamid Q, Martin J G. The epidermal growth factor receptor mediates allergic airway remodeling in the rat. *Eur Respir J* 2008; 32: 1213-1223.
37. Zhen G, Park S W, Nguyenvu L T, Rodriguez M W, Barbeau R, Paquet A C, Erle D J. IL-13 and epidermal growth factor receptor have critical but distinct roles in epithelial cell mucin production. *Am J Respir Cell Mol Biol* 2007; 36: 244-253.
38. Marone R, Cmiljanovic V, Giese B, Wymann M P. Targeting phosphoinositide 3-kinase-moving towards therapy. *Biochim Biophys Acta* 2008; 1784: 159-185.
39. Kwak Y G, Song C H, Yi H K, Hwang P H, Kim J S, Lee K S, Lee Y C. Involvement of PTEN in airway hyperresponsiveness and inflammation in bronchial asthma. *J Clin Invest* 2003; 111: 1083-1092.
40. Myou S, Leff A R, Myo S, Boetticher E, Tong J, Meliton A Y, Liu J, Munoz N M, Zhu X. Blockade of inflammation and airway hyperresponsiveness in immunesensitized mice by dominant-negative phosphoinositide 3-kinase-TAT. *J Exp Med* 2003; 198: 1573-1582.
41. Duan W, Aguinaldo Datiles A M K, Leung B P, Vlahos C J, Wong W S F. An anti-inflammatory role of a phosphoinositol 3-kinase inhibitor LY294002 in a mouse asthma model. *Int Immunopharmacol* 2005; 5: 495-502.
42. Lee K S, Lee H K, Hayflick J S, Lee Y C, Puri K D. Inhibition of phosphoinositide 3-kinase □ attenuates allergic airway inflammation and hyperresponsiveness in murine asthma model. *FASEB J* 2006; 20: 455-465.
43. Doukas J, Eide L, Stebbins K, Racanelli-Layton A, Dellamary L, Martin M, Dneprovskaia E, Noronha G, Soll R, Wrasidlo W, et al. Aerosolized phosphoinositide 3-kinase□/□ inhibitor TG100-115 [3-[2,4-d]amino-6-(3-hydroxyphenyl)pteridin-7-yl]phenol] as a therapeutic candidate for asthma and chronic obstructive pulmonary disease. *J Pharmacol Exp Ther* 2009; 328: 758-765.
44. Fujitani Y, Trifilieff. In vivo and in vitro effects of SAR 943, a rapamycin analogue, on airway inflammation and remodeling. *Am J Respir Crit Care Med* 2003; 167: 193-198.
45. Birrell M A, Mardaker E, Wong S, McCluskie K, Cately M, De Alba J, Newton R, Haj-Yahia S, Pun K T, Watts C J, et al. IκB kinase-2 inhibitor blocks inflammation in human airway smooth muscle and a rat model of asthma. *Am J Respir Crit Care Med* 2005; 172: 962-971.
46. Kelly-Welch A E, Hanson E M, Boothby M R, Keegan A D. Interleukin-4 and interleukin-13 signaling connections maps. *Science* 2003; 300: 1527-1528.
47. Sano M, Leff A R, Myou S, Boetticher E, Meliton A Y, Learoyd J, Lambertino A T, Munoz N M, Zhu X. Regulation of interleukin-5-induced β2-integrin adhesion of human eosinophils by phosphoinositide 3-kinase. *Am J Respir Cell Mol Biol* 2005; 33: 65-70.
48. Meyer-Hoffert U, Lezcano-Meza D, Bartels J, Montes-Vizuet A R, Schroder J M, Teran LM. Th2- and to a lesser extent Th1-type cytokines upregulate the production of both CXC (IL-8 and gro-alpha) and CC(RANTES, eotaxin, eotaxin-2, MCP-3 and MCP-4) chemokines in human airway epithelial cells. *Int Arch Allergy Immunol* 2003; 131: 264-271.
49. Kumar A, Takada Y, Boriek A M, Aggarwal B B. Nuclear factor-KB: Its role in health and disease. *J Mol Med* 2004; 82: 434-448.
50. Ali K, Bilancio A, Thomas M, Pearce W, Gilfillan A M, Tkaczyk C, Kuehn N, Gary A, Giddings J, Peskett E, et al. Essential role for the p110δ phosphoinositide 3-kinase in the allergic response. *Nature* 2004; 431: 1007-1011.
51. Kitaura J, Asai K, Maeda-Yamamoto, Kawakami Y, Kikkawa U, Kawakami T. Akt-dependent cytokine production in mast cells. J Exp Med 2000; 192: 729-739.
52. Webb D C, McKenzie A N, Foster P S. Expression of the Ym2 lectin-binding protein is dependent on interleukin (IL)-4 and IL-13 signal transduction: Identification of a novel allergy-associated protein. *J Biol Chem* 2001; 276: 41969-41976.
53. Ricciardolo F L M, Sterk P J, Gaston B, Folkerts G. Nitric oxide in health and disease of the respiratory system. *Physiol Rev* 2004; 84: 731-765.
54. Lane C, Knight D, Burgess S, Franklin P, Horak F, Legg J, Moeller A, Stick S. Epithelial inducible nitric oxide synthase activity is the major determinant of nitric oxide concentration in exhaled breath. *Thorax* 2004; 59: 757-760.
55. Sakai K, Suzuki H, Oda H, Akaike T, Azuma Y, Murakami T, Sugi K, Ito T, Ichinose H, Koyasu S, Shirai M. Phosphoinositide 3-kinase in nitric oxide synthesis in macrophage. Critical dimerization of inducible nitric-oxide synthase. *J Biol Chem* 2006; 281: 17736-17742.
56. Halayko A J, Kartha S, Stelmack G I, McConville J, Tam J, Camoretti-Mercado B, Forsythe S M, Hershenson M B, Solway J. Phosphatidylinositol-3 kinase/mammalian target of rapamycin/p70S6K regulates contractile protein accumulation in airway myocyte differentiation. *Am J Respir Cell Mol Biol* 2004; 31: 266-275.
57. Zhou L, Goldsmith A M, Bentley J K, Jia Y, Rodriguez M I, Abe M K, Fingar D C, Hershenson M B. 4E-binding protein phosphorylation and eukaryotic initiation factor-4E release are required for airway smooth muscle hypertrophy. *Am J Respir Cell Mol Biol* 2005; 33: 195-202.
58. Farghaly H S M, Blagbrough I S, Medina-Tato D A, Watson M L. Interleukin 13 increases contractility of murine tracheal smooth muscle by a phosphoinositide 3-kinase p110□-dependent mechanism. *Mol Pharmacol* 2008; 73: 1530-1537.

The invention claimed is:
1. A method of treating or controlling chronic obstructive pulmonary disease (COPD) comprising administering an effective dose of an artemisinin derivative of formula (2):

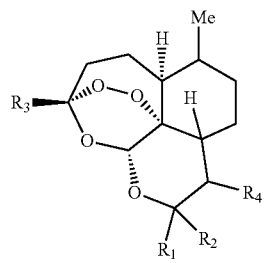

wherein $R_1$ and $R_2$ taken together form a carbonyl (═O), and $R_3$ and $R_4$ are independently H, or an optionally substituted group selected from a substituted or non-substituted alkyl, a substituted or non-substituted aryl, a substituted or non-substituted heteroaryl, a substituted or non-substituted arylalkyl, and a substituted or non-substituted heteroarylalkyl or a pharmaceutically acceptable salt or ester thereof; or wherein $R_1$ is H, and $R_2$ is —OA, wherein A is H or an optionally substituted group selected from a substituted or non-substituted alkyl, a substituted or non-substituted aryl, a substituted or non-substituted heteroaryl, a substituted or non-substituted arylalkyl, and a substituted or non-substituted heteroarylalkyl; or a pharmaceutically acceptable salt or ester thereof and $R_3$ and $R_4$ are independently H or an optionally substituted group selected from a substituted or non-substituted alkyl, a substituted or non-substituted aryl, a substituted or non-substituted heteroaryl, a substituted or non-substituted arylalkyl, and a substituted or non-substituted heteroarylalkyl; or a pharmaceutically acceptable salt or ester thereof.
2. The method of claim 1, wherein $R_1$ and $R_2$ taken together form a C1-C6 carbonyl and $R_3$ and $R_4$ are independently H or an optionally substituted C1-C10 alkyl.

3. The method of claim 1 wherein the artemisinin derivative is selected from the group consisting of artemisinin, dihydroartemisinin, artemether, artemotil, artelinic acid, arteether, and artesunate.

4. The method of claim 3 wherein the derivative is artesunate.

5. The method claims 1 further comprising administering an effective amount of steroids in combination with the derivative.

6. The method of claim 5 wherein the steroid is a corticosteroid.

7. The method of claim 5 wherein the steroid comprises Budesonide, Fluticasone, Ciclesonide, or Beclomethasone Dipropionate.

8. The method any one of claim 1 further comprising administering an effective amount of a $\beta_2$ agonist in combination with the derivative.

9. The method of claim 8, wherein the $\beta_2$ agonist comprises: salbutamol; albuterol, terbutaline, salmeterol, or formoterol.

10. The method of claim 1 further comprising administering an effective amount of an anticholinergic in combination with the derivative.

11. The method of claim 10 wherein the anticholinergic comprises Ipratropium.

* * * * *